ered under 35

(12) United States Patent
Stering

(10) Patent No.: US 10,473,677 B2
(45) Date of Patent: Nov. 12, 2019

(54) RELIABILITY OF AN INTEGRITY OR LEAK TEST OF A SAMPLE

(71) Applicant: Sartorius Stedim Biotech GmbH, Goettingen (DE)

(72) Inventor: Magnus Stering, Le mesnil le roi (FR)

(73) Assignee: Sartorius Stedim Biotech GmbH (DE)

( * ) Notice: Subject to any disclaimer, the term of this patent is extended or adjusted under 35 U.S.C. 154(b) by 192 days.

(21) Appl. No.: 15/666,626

(22) Filed: Aug. 2, 2017

(65) Prior Publication Data

US 2018/0038880 A1 Feb. 8, 2018

(30) Foreign Application Priority Data

Aug. 8, 2016 (EP) ..................................... 16290148

(51) Int. Cl.
*G01M 3/26* (2006.01)
*G01N 15/08* (2006.01)
*G01N 35/00* (2006.01)
*G01M 3/02* (2006.01)

(52) U.S. Cl.
CPC ...... *G01N 35/00623* (2013.01); *G01M 3/027* (2013.01); *G01M 3/26* (2013.01); *G01N 15/08* (2013.01); *G01N 2015/084* (2013.01)

(58) Field of Classification Search
CPC .......... G01M 3/02; G01M 3/027; G01M 3/26; G01N 15/00; G01N 15/08; G01N 35/00; G01N 35/00623; G01N 2015/084
See application file for complete search history.

(56) References Cited

U.S. PATENT DOCUMENTS

| | | | | |
|---|---|---|---|---|
| 6,311,548 B1 * | 11/2001 | Breidenbach | ...... | F02M 25/0809 73/114.39 |
| 10,161,243 B2 * | 12/2018 | Franklin | ................. | G01M 3/28 |
| 2001/0032494 A1 * | 10/2001 | Greszler | ............ | A61B 1/00057 73/40 |
| 2007/0060791 A1 | 3/2007 | Kubach | | |
| 2011/0010115 A1 * | 1/2011 | Bosshart | ............... | G01M 3/002 702/51 |

(Continued)

FOREIGN PATENT DOCUMENTS

JP 2002-267567 9/2002

OTHER PUBLICATIONS

European Search Report dated Jan. 10, 2017.

*Primary Examiner* — Nguyen Q. Ha
(74) *Attorney, Agent, or Firm* — Gerald E. Hespos; Michael J. Porco; Matthew T. Hespos

(57) ABSTRACT

A method for improving reliability of an integrity or leak test includes determining at least one first parameter indicative of: a first volume of a sample, a first temperature of the sample, a first pressure of the sample and/or a first assessment of integrity of the sample. The method further determines at least one second parameter indicative of a deviation from the first parameter and at least one third parameter indicative of a second assessment of the integrity of the sample. The second assessment provides an indication of a passed or failed test. The method further determines whether the deviation has an impact on the indication of the second assessment. When the deviation is determined to have an impact on the indication of the second assessment, the method comprises identifying a possibility that the indication of the second assessment is incorrect.

14 Claims, 38 Drawing Sheets

(56) References Cited

U.S. PATENT DOCUMENTS

| | | | |
|---|---|---|---|
| 2012/0150455 A1* | 6/2012 | Franklin | G01M 3/2815 |
| | | | 702/51 |
| 2017/0254719 A1* | 9/2017 | Franklin | G01M 3/26 |

* cited by examiner

THERMAL EXPANSION COEFFICIENTS FOR
SOME MATERIALS MEASURED AT 25° C

| MATERIAL | $(10^{-6} M/(M\ K))^*$ |
|---|---|
| ALUMINUM | 22.2 |
| POLYETHYLENE (PE) | 200 |
| POLYETHYLENE TEREPHTHALATE (PET) | 59.4 |
| POLYPROPYLENE (PP), UNFILLED | 100 - 200 |
| POLYSTYRENE (PS) | 70 |
| POLYSULFONE (PSO) | 55.8 |
| POLYURETHANE (PUR), RIGID | 57.6 |
| POLYVINYL CHLORIDE (PVC) | 50.4 |
| STEEL | 12.0 |
| STAINLESS STEEL | 9.9 - 17.3 |

FIG. 5

| TIME (SEC) /1701 | TEMPERATURE SURROUNDING (C°) /1703 | SC4 TEST VALUE (ML/MIN) /1705 |
|---|---|---|
| 176 | 22.29 | 10.3 |
| 195 | 34.84 | 10.4 |
| 199 | 39.94 | 10.5 |
| 202 | 42.44 | 10.6 |
| 205 | 45.1 | 10.7 |
| 213 | 50.97 | 10.7 |
| 222 | 56.16 | 10.6 |
| 229 | 59.48 | 10.4 |
| 235 | 61.49 | 10.1 |
| 241 | 63.11 | 9.9 |
| 248 | 65.07 | 9.7 |
| 255 | 66.05 | 9.4 |
| 262 | 67.04 | 9.1 |
| 270 | 68.09 | 8.8 |
| 279 | 69.91 | 8.3 |
| 290 | 69.8 | 7.9 |
| 300 | 70.76 | 7.5 |

AMBIENT TEMPERATURE 22.29 °C

FIG. 14

| TIME (SEC) ⌐1901 | TEMPERATURE SURROUNDING (C°) ⌐1903 | SC4 TEST VALUE (ML/MIN) ⌐1905 |
|---|---|---|
| 181 | 22.3 | 11.2 |
| 198 | 34.5 | 11.6 |
| 202 | 34.8 | 12 |
| 204 | 34.91 | 12.2 |
| 208 | 34.94 | 12.4 |
| 212 | 34.88 | 12.3 |
| 215 | 34.88 | 12.2 |
| 223 | 34.76 | 11.6 |
| 231 | 34.77 | 10.5 |
| 240 | 34.85 | 9.7 |
| 251 | 34.82 | 8.7 |
| 273 | 34.8 | 7.5 |
| 288 | 34.78 | 6.8 |
| 300 | 34.76 | 6.3 |

AMBIENT TEMPERATURE 22.30 °C

FIG. 16

| | A | B | C | D | E | F |
|---|---|---|---|---|---|---|
| 1 | TEST PRESSURE | 2500 MBAR | | | | |
| 2 | DOWNSTREAM VOLUME | 600 ML | | | | |
| 3 | DIFFUSION RATE | 18 ML/MIN | | | | |
| 4 | TEST TIME INCLUDING STABILIZATION (MIN) | NORMAL CUMULATED DIFFUSION OPEN VALVE | CUMULATED DIFFUSION CLOSED VALVE | ACTUAL DIFFUSION (INSTANT) CLOSED VALVE | CUMULATED PRESSURE INCREASE DOWNSTREAM SIDE (MBAR) | REDUCTION OF DIFFUSION (%) VS INITIAL |
| 5 | 0 | 18 | 18 | 18 | 0 | 0% |
| 6 | 1 | 17,95 | 17,89 | 17,78 | 30,0 | 1,2% |
| 7 | 2 | 17,93 | 17,78 | 17,57 | 59,6 | 2,4% |
| 8 | 3 | 17,93 | 17,68 | 17,36 | 88,9 | 3,6% |
| 9 | 4 | 17,93 | 17,57 | 17,15 | 117,9 | 4,7% |
| 10 | 5 | 17,93 | 17,47 | 16,95 | 146,4 | 5,9% |
| 11 | 6 | 17,93 | 17,36 | 16,74 | 174,7 | 7,0% |
| 12 | 7 | 17,93 | 17,26 | 16,54 | 202,6 | 8,1% |
| 13 | 8 | 17,93 | 17,16 | 16,34 | 230,2 | 9,2% |
| 14 | 9 | 17,93 | 17,06 | 16,15 | 257,4 | 10,3% |
| 15 | 10 | 17,93 | 16,96 | 15,95 | 284,3 | 11,4% |
| 16 | 11 | 17,93 | 16,86 | 15,76 | 310,9 | 12,4% |

FIG. 19

REAL TIME CORRECTION ☐  OR POST-TEST CORRECTION ☑

OR RISK ASSESSMENT ☐

AND TREND ANALYSIS ☑

FIG. 27

SYSTEM TO BE TESTED: _BAG 50L_  ▽ AUTOMATIC

N° OF EXTERNAL TEMPERATURE SENSORS:__

N° OF INTERNAL SAMPLE TEMPERATURE SENSORS:__

N° OF EXTERNAL HUMIDITY SENSORS:__

SYSTEM TO BE TESTED: BAG 50L 🔍 ▽ AUTOMATIC
• FLEXBOY 50L WITH CONSTRAINING PLATES
N° OF EXTERNAL TEMP • STR 50L INSTALLED BAG

N° OF INTERNAL SAMPLE TEMPERATURE SENSORS:__

N° OF EXTERNAL HUMIDITY SENSORS:__

FIG. 29

RELIABILITY OF AN INTEGRITY OR LEAK TEST OF A SAMPLE

BACKGROUND

Field

The technical field of the present application is quality assurance related testing in the pharmaceutical industry and/or the biotechnology industry. Quality assurance testing may be performed in the interest of the health and safety of patients. In particular, the present application relates to performing an integrity or leak test of a sample. The sample may be a container such as a filter, a crossflow cassette, a single use bag or a tank or vessel for storing.

Related Art

An integrity test or leak test may be used to check the integrity of a barrier for example a barrier for microbiological contamination, such as a microporous membrane, a plastic film, a wall of a container, or single use bag.

In particular, the sample may have an upstream side and a downstream side, where the upstream side is not sterile and the downstream side is sterile. The integrity test may be used to check for cracks, or changes in the pore structure of a filter element of the filter during the course of a pharmaceutical (e.g. a biopharmaceutical) process. At the start of the integrity test, the filter may be disconnected from the pharmaceutical process or the filter may be tested in the process (in-line). After the start of the test, the filter may be pressurized to a specified value on the upstream side. Various types of integrity tests may be performed, for example in a bubble point test, applied test pressure is raised successively while monitoring to determine a disproportionate increase in diffusion. An assessment of the integrity of the sample may be provided as a result of the test. The assessment may be provided as a rate of flow or a pressure value. The assessment may be compared to a specified limit value of the sample (e.g. supplied by a manufacturer of the sample) to determine whether the integrity test is a passed test or a failed test.

In the context of a leak test, the sample may be a container such as a single use bag.

The assessment of the integrity of the sample may correspond to fluid pressure within the sample. The fluid pressure within the sample may enable a determination of a leakage amount, and accordingly whether there is a leak based on the leakage amount. A passed test may occur when there is no leak, and a failed test may occur when there is a leak.

An integrity test or a leak test may be carried out by assessing the integrity of the sample.

An integrity test or a leak test may determine whether a sample will fulfill agreed upon specifications. The integrity test may determine microbiological performance of a sample. In particular, when an integrity assessment provides an indication of a passed test, the sample is likely (e.g. 95% or more, preferably 98% or more) to perform as expected. A failed test may indicate cracks or changes in the pore structure of a filter element of the sample.

A leak test of a sample may be understood to give the indication of whether the sample has a breach e.g. a hole or pinhole above a defined size. A passed test indicates there is no hole or breach above the defined size.

The reliability of both tests depends also on the quality management of the manufacturer of the sample.

Conventional integrity testing and leak testing may be unreliable. In some cases, the integrity test or leak test is performed under the assumption that neither the volume nor the temperature of the sample changes during the test period. The test period may begin at the start of the test (e.g. time $t_0$) and end when the test is completed. The test may be considered completed at a specified duration from the start of the test. The test period may comprise the whole integrity or leak test. The test period may be divided into a pressure increase phase, a stabilization phase, an optional volume determination, a second stabilization phase following the volume determination, and a measurement phase. The measurement phase of the test may start after a certain period of pressure stabilization and may end after the specified duration or when an assessment of the integrity of the sample (e.g. a test value) is considered stable and reliable (e.g. the test apparatus may interrupt the test before the completed test time based on a stable test value or the user may extend the test beyond the specified duration in order to obtain a stable assessment).

The test period may extend from time $t=0$ s to a time from one to five minutes after the start of the test. Various test periods are possible depending upon the nature of the integrity test and the type of the sample.

It is a problem to account for the influence of volume changes (i.e. deviations) in a sample, especially in a single-use sample, for example a flexible bag or a plastic filter capsule, during a leak test or an integrity test. Volume changes of the sample may result from expansion or contraction of the material with which the sample is made, e.g. plastic such as polypropylene, ethylene vinyl acetate copolymer (EVA), ethyl vinyl alcohol (EVOH) or polyethylene.

A temperature increase of an environment of the sample may cause a temperature increase of the sample. Accordingly, if there is a temperature increase of the environment of the sample, the sample may expand, i.e. the volume of the sample may increase. The increase in the volume of the sample will result in a decrease of the pressure inside the sample if no further gas or liquid is injected. Further, there may be fluid (e.g. a test gas) inside the sample. Heat transfer from the environment around the sample into the fluid within the sample will heat up the fluid and thus increase the pressure within the sample.

It may be a problem to account for a delay in heat transfer from or to the environment of the sample to or from the sample when performing an integrity test or leak test. The heat transfer may result from an increase in the temperature of the environment or a decrease in the temperature of the environment. It may also be a problem to account for expansion or contraction of the sample resulting from the heat transfer when performing the test. The compensation may be carried out by providing an alarm or error message, or mitigating the heat transfer or change in volume of the sample. In particular, a determination may be made as to whether a deviation in the environmental conditions of the sample has an impact on an assessment of the integrity of the sample, i.e. the test result. An incorrect (i.e. false) passed test result may put the life of a patient in danger.

An integrity test or leak test may verify that no damage to the sample has occurred. For example, damage to the sample may occur during transportation, storage, installation of the sample into a holder or following procedures such as steam sterilization, gamma irradiation or chemical cleaning prior to use of the sample.

An assessment of the integrity of a sample carried out in the integrity test or the leak test may be referred to as a test result. The assessment of the integrity of the same may also determine whether the sample is leak-proof. An indication that the assessment is incorrect may be a false passed test or a false failed test. In other words, the indication of the assessment may incorrectly indicate a passed test or the indication of the assessment may incorrectly indicate a failed test.

A further way of improving the reliability of an integrity test or a leak test may be detecting an incorrect test setup while performing the test. An example of an incorrect test setup is a closed downstream valve on the sample. According to the example, the closed downstream valve generates increased downstream pressure as fluid diffuses through the sample and towards the downstream valve. Increased downstream pressure means reduced differential pressure resulting in a decreased rate of diffusion. Failure to account for the incorrect test setup may result in an incorrect indication from an assessment of the integrity of the sample taken during the test period. In the case were an indication of a passed test is incorrect, the indication may put a patient's life in danger.

The assessment of the integrity of the sample may be taken by determining parameters indicative of the assessment of the integrity of the sample.

Conventional approaches recognize that changes in the temperature of the environment of the sample have an impact on assessments of the integrity of the sample. This can be seen from the ideal gas law:

$$pV = nRT$$

where:
P is the absolute pressure of the gas,
V is the volume of the gas,
n is the amount of substance of gas (in moles),
R is the ideal gas constant, equal to the product of the Boltzmann constant and the Avogadro constant,
T is the temperature of the gas (in Kelvin).

Conventionally, a change or deviation in the temperature of the environment of the sample may cause incorrect test results. In particular, assessments of the integrity of the sample may provide an incorrect indication of a passed test or a failed test. The incorrect indication may be due to the change in temperature of the environment of the sample. Accordingly, users performing integrity or leak tests are typically instructed to ensure that a specified environmental temperature variation is maintained. The specified environmental temperature variation is generally from +/-0K to +/-2K. A variation of +/-0K is normally impossible to achieve. In other words, it is generally impossible to ensure that the temperature of the sample does not vary, at least to some degree, for the duration of the test. In some cases, a specified environmental temperature variation of +/-2K may not be strict enough since a temperature variation of 1K inside the entire volume of the sample may, for example, correspond to a 100% variation of the assessment of the integrity of the sample. In other cases, a specified environmental variation of +/-2K may be too strict if the sample is for example confined in an insulating holder.

Conventionally, it is considered that a temperature increase in the environment of the sample increases the pressure of the sample and decreases the determined rate of diffusion, with the possibility of providing a false indication of a passed test. A temperature decrease on the other hand is conventionally considered to reduce the pressure within the sample and thereby increase the determined rate of diffusion, with the possibility of providing an incorrect indication of a failed test.

Experimental data discussed in the present application shows that reality is more complex than the conventional understanding. Although much of the experimental data described in the present application was obtained in the context of a diffusion test (forward flow test), the results are applicable to other types of integrity tests (e.g. bubble tests, water intrusion tests, water flow tests) as well as leak tests.

SUMMARY

According to an aspect, a computer implemented method for improving the reliability of an integrity or a leak test of a sample is provided. The method comprises determining at least one first parameter indicative at least one of the following:
a first volume of the sample;
a first temperature of the sample;
a first pressure of the sample; and
a first assessment of the integrity of the sample.

The at least one first parameter is determined under specified temperature conditions.

The method further comprises determining at least one second parameter indicative of a deviation from the first parameter. The method further comprises determining, after determining the at least one second parameter, at least one third parameter indicative of a second assessment of the integrity of the sample, wherein the second assessment provides an indication of a passed test or a failed test. The method further comprises determining whether the deviation has an impact on the indication of the second assessment. When the deviation is determined to have an impact on the indication of the second assessment, the method further comprises identifying a possibility that the indication of the second assessment is incorrect.

Specified temperature conditions may be defined according to a reference temperature (e.g. room temperature) and a maximum variation from the reference temperature. The reference temperature and the maximum variation from the reference temperature may be determined according to characteristics of the sample. Alternatively, the specified temperature conditions may be initial temperature conditions at the beginning of the test or stable temperature conditions that remain constant for a predetermined period of time.

The deviation may also be described as a variation or change. The at least one first parameter may be determined via a temperature sensor, such as a thermistor. In some cases, the at least one first parameter includes a temperature of the sample or another measurement indicative of a temperature of the sample. For example, a measurement of the kinetic energy of the sample may provide an indication of the temperature.

The first volume of the sample may be determined according to a correspondence table. The correspondence table may describe relationships between temperatures of the sample and volumes of the sample. In particular, the correspondence table may show different volumes of the sample at various temperatures, i.e. volume change from one temperature to another. The correspondence table for the sample may be determined experimentally. Each type of sample may have its own correspondence table showing different volumes of the sample at various temperatures, i.e. volume changes of the sample in response to temperature changes. In particular, each correspondence table may be derived by performing an integrity test or leak test of the sample and recording volume changes of the sample in response to temperature changes or by measuring the weight of the sample after filling the sample (e.g. a filter element of a filter) with water at various temperatures.

Each type of sample may be associated with a set of characteristics, e.g. material composition and/or maximum rate of diffusion.

The deviation may comprise a deviation from the first temperature of the sample. The deviation from the first temperature of the sample may cause a corresponding deviation from the first volume of the sample.

The corresponding deviation from the first volume of the sample may be determined according to the correspondence table described above, or from other means of recording relationships between changes in temperature of the sample and corresponding changes in volume of the sample.

The first assessment of the integrity of the sample may be determined when the sample has the first volume and the first temperature. The first assessment of the integrity of the sample may be determined using a test apparatus, such as the Sartocheck 3.

Determining the parameters (e.g. the first parameter, the second parameter and the third parameter) may comprise indirectly determining at least one of the first volume, the first temperature, the first pressure, and the first assessment of the integrity of the sample by measuring other properties of the sample. Such measurements may be carried out using at least one of the following: the temperature sensor, a humidity sensor, a tension sensor, a pressure sensor.

The pressure sensor may be implemented as part of a tension sensor. In particular, the pressure sensor and the tension sensor may be implemented using a capsular tension ring.

In some cases, each parameter is determined via a sensor integrated with the sample, attached to the sample, or in the environment of the sample.

Each parameter may be determined during the test, e.g., based on measurements taken during the test. The at least one first parameter and/or the at least one second parameter may be based on a temperature of the sample or another measurement indicative of the temperature.

The first temperature of the sample may be indicative of the first volume of the sample. The deviation from the first parameter may be determined based on temperature measurements of the sample.

Each parameter may be determined based on a measurement of the sample or a measurement of the environment of the sample. Each parameter may be based on measurements taken during the test. The at least one first parameter and/or the at least one second parameter may be based on a temperature of the sample or a measurement indicative of the temperature. The first temperature of the sample may be indicative of the first volume of the sample. The deviation from the first volume may be determined based on a temperature or a tension of the sample, or measurements indicative of the temperature or the tension.

For example, the at least one first parameter may include the first assessment of the integrity of the sample and the at least one second parameter may be indicative of a deviation from the first assessment of the integrity of the sample. Alternatively, the first parameter may be indicative of a first temperature of the sample and the second parameter may be indicative of a deviation from the first temperature. The deviation in temperature may also indicate a deviation in volume, even if a first volume of the sample is not known. A deviation in the volume of the sample may also be indicated by a change in the pressure of the sample.

Multiple, e.g. at least three, parameters may be indicative of the first assessment of the integrity of the sample.

Multiple, e.g. at least two, parameters may be indicative of the deviation from the first assessment of the integrity of the sample. Multiple parameters may be indicative of the second assessment of the integrity of the sample. The multiple parameters may include a determined change in a pressure of the sample. The determined change in the pressure of the sample may be a change in the speed at which the pressure of the sample decreases. The determined change in pressure may be used to calculate a rate of diffusion of the sample. Each assessment of the integrity of the sample may be a rate of diffusion of the sample. In other words, the integrity of the sample may be assessed by a calculated rate of diffusion of the sample.

The determination of whether the deviation has an impact on the indication may be based on one or more of the following: a rate of heat transfer to or from the sample, a change in the volume of the sample with respect to the first volume.

The rate of heat transfer to or from the sample and/or the change in the volume of the sample with respect to the first volume may be determined at the same time that the second assessment of the integrity of the sample is determined.

The rate of heat transfer to or from the sample and/or the change in volume of the sample may be determined based on one or more of the following:
  characteristics of the sample,
  localization of the deviation from the first temperature of
     the sample,
  whether the sample is a bag or a filter including the
     housing and a filter element,
  when the sample is a filter, an intermediate volume
     between the filter element and an inner wall of the
     housing,
  whether the sample is encapsulated in a holder,
  when the sample is encapsulated in the holder, the com-
     position and position of the holder,
  a humidity of an environment of the sample,
  a tension of the sample.

The environment of the sample may be a three-dimensional region less than one meter away from the sample in any direction, or the environment of the sample may be defined by the holder.

The second assessment may be an ending assessment taken at the end of a test period.

Determining whether the deviation has an impact on the indication of the second assessment may comprise determining a second volume of the sample. Determining whether the deviation has an impact on the indication of the second assessment may further comprise determining a volume change that quantifies the difference between the second volume of the sample and the first volume of the sample, and determining a rate of heat transfer to or from the sample. The second volume of the sample and the rate of heat transfer to or from the sample may be determined when the second assessment is determined.

The impact on the indication of the second assessment may comprise at least one of an impact resulting from the volume change and an impact resulting from the rate of heat transfer to or from the sample.

The method may further comprise establishing, before the test, characteristics of the sample. The at least one third parameter indicative of the second assessment may be determined at a specified time. The method may further comprise receiving, for the specified time and according to at least one of the characteristics of the sample, a maximum expected change in the assessment of the integrity of the sample under specified temperature conditions. Determining whether the deviation has an impact on the indication of the second assessment may further comprise, when the second assessment of the integrity of the sample deviates from the first assessment of the integrity of the sample by a quantity greater than the maximum expected change, determining that the deviation has an impact on the indication.

When the second assessment of the integrity of the sample deviates from the first assessment of the integrity of the sample by quantity greater than the maximum expected change, the method may further comprise determining that there is a possibility of an incorrect test setup.

When a possibility that the indication of the second assessment is incorrect is identified (e.g. there is a possibility of an incorrect test setup), a number of further actions may be taken. In particular, an error message may be generated. In addition or alternatively, steps may be taken to mitigate or correct the second assessment.

The characteristics of the sample may include thermal characteristics. The thermal characteristics may comprise one or more of the following: a coefficient of thermal expansion, a specific heat, a thermal inertia.

The characteristics of the sample may include design characteristics. The design characteristics may include at least one of the following: dimensions, geometry, material composition, a wall thickness of the sample, a type of the sample, a maximum rate of diffusion, a maximum pressure and, if the sample is a filter, a pore size of a filter element of the sample.

Examples of material composition of the sample (e.g. a filter element of a filter) include polypropylene, polyethylene, polycarbonate, polyetherimide other types of plastic, composite material as well as stainless steel. The supporting structure of a filter element can be made for example from polypropylene, polyamide or PTFE. The membrane can be made for example of polyethersulfon, PVDF, PTFE, cellulose acetate, regenerated cellulose and nylon. Bags or containers can be made out of polypropylene, ethylene vinyl acetate copolymer (EVA), ethyl vinyl alcohol (EVOH), polyethylene of various densities as well as glass.

For filter elements the pore size may range from 10 nm to 5 μm. and for crossflow cassettes from 100 kD to 1.0 μm, preferably from 1000 kDa to 0.45 μm.

The first assessment of the integrity of the sample may be a pressure of the sample (e.g. within the sample) or a rate of diffusion of the sample. The second assessment of the integrity of the sample may be a pressure of the sample (e.g. within the sample) or a rate of diffusion of the sample (e.g. within the sample).

The test may comprise periodically monitoring at least one of the temperature, pressure, and humidity of an environment of the sample.

The method may comprise carrying out the integrity test or the leak test during performance of an industrial process, particularly a pharmaceutical process.

The sample may be a bag or a filter (i.e. a filter capsule), particularly a sterilizing filter. The filter may include a housing and an element inside the housing. The element may be a filter cartridge. The element may be a membrane having a pore size.

When the test is an integrity test, the test may include one or more of the following: a diffusion test, a pressure drop test, a bubble point test, a water intrusion test, an aerosol challenge test.

The second assessment may be determined at the end of the test period.

According to yet another aspect a computer program product may be provided. The computer program product may comprise computer readable instructions, which when executed on a computer system, cause the computer system to perform operations as described above.

According to yet another aspect, a computer system for improving the reliability of an integrity test or a leak test of a sample is provided. The system comprises a plurality of sensors arranged around or within the sample. The sensors are operable to determine at least one first parameter indicative of at least one of the following:

a first volume of the sample;
a first temperature of the sample;
a first pressure of the sample;
a first assessment of the integrity of the sample;

The at least one first parameter is determined under specified temperature conditions The sensors are operable to determine at least one second parameter indicative of a deviation from the first parameter. After determining the at least one second parameter, the sensors are operable to determine at least one third parameter indicative of a second assessment of the integrity of the sample. The second assessment provides an indication of a passed test or a failed test.

The system further comprises a processor. The processor is operable to determine whether the deviation has an impact on the indication of the second assessment. When the deviation is determined to have an impact on the indication of the second assessment, the processor identifies a possibility that the indication of the second assessment is incorrect.

The sensors may comprise one or more of the following: the temperature sensor, the humidity sensor, the tension sensor, the pressure sensor.

Subject matter of the present application may be implemented as software combined with hardware for improving the reliability of integrity test results or leak test results. A leak test may be carried out with a container or bag, e.g. a single use bag. An integrity test may be carried out using a sterilizing filter. The subject matter of the present application may be particularly applicable in situations in which environmental temperature variations occur. The environmental temperature variations may result in the determination of a parameter indicative of a deviation from one or more of a first volume, a first temperature, a first assessment of the integrity of the sample being tested. The first assessment of the integrity of the sample may indicate whether the sample leaks, i.e. whether the sample is leak-proof.

The parameter indicative of the deviation may be determined by measuring a change in the environmental conditions of the test. The impact of the deviation may be based on whether the change in environmental conditions is localized to a part of the sample or effects the entire sample.

The determination of whether the deviation has an impact on the indication of the assessment may be based on thermal characteristics of the sample, or the efficiency of heat transfer to or from the sample wall. The determination of whether the deviation has an impact on the indication of the assessment of integrity may also be based on environmental humidity. Other factors may include the geometry of the sample or the speed and amount of thermal expansion/contraction of the sample according to localized environmental deviations. Further factors may be thermal capacity and/or thermal conductivity of the sample wall, thus taking into account the material composition of the sample and the thickness of the sample wall. Another factor affecting the determination of whether the deviation has an impact on the indication may be the maximum expected change in the assessment of the integrity of the sample under stable temperature conditions, e.g. temperature conditions that have been corrected for stability.

Each assessment of the integrity of the sample may provide an indication of a passed test or a failed test. If the deviation is determined to have an impact on the indication of the assessment, a possibility that the indication of the assessment is incorrect may be identified. If such a possibility is identified, an error message may be generated. Alternatively, the indication of the second assessment or the second assessment itself may be corrected. The correction of the second assessment may be carried out based on data specific to the sample, e.g. stored in a database. The correction may be carried out in real time or at the end of the test. An error message may be generated if the impact of the deviation goes beyond what can be corrected.

When an assessment of the integrity of the sample determined during the test deviates from an assessment of the integrity of the sample obtained under specified temperature conditions by a quantity greater than a maximum expected change, an error message may be generated. This may be useful for detecting an incorrect setup, e.g. a closed downstream valve.

Advantageously, aspects of the disclosed subject matter may avoid false passed tests results, false failed test results or unnecessarily strict test conditions. Accordingly, quality assurance of leak and integrity test procedures may be increased.

False passed test results may put a patient's life in danger. False failed test results may cause a shortage of a pharmaceutical being produced because products are unnecessarily discarded or held for further testing.

The subject matter described in this application can be implemented as a method or on a device, possibly in the form of one or more computer program products. Such computer program products may cause a data processing apparatus to perform one or more operations described in the application.

The subject matter described in the application can be implemented in a data signal or on a machine readable medium, where the medium is embodied in one or more information carriers, such as a CD-ROM, a DVD-ROM, a semiconductor memory, or a hard disk. The data signal may be retrievable from the Internet.

In addition, the subject matter described in the application can be implemented as a system including a processor, and a memory coupled to the processor. The memory may encode one or more programs to cause the processor to perform one or more of the methods described in the application. Further subject matter described in the application can be implemented using various machines.

Details of one or more implementations are set forth in the exemplary drawings and description below. Other features will be apparent from the description, the drawings, and from the claims.

BRIEF DESCRIPTION OF THE DRAWINGS

FIG. 5 shows thermal expansion coefficients for some materials determined at 25° C.

FIG. 14 shows assessments of the integrity of a sample resulting from localized temperature deviations.

FIG. 16 shows integrity assessments of the sample taken after a temperature deviation that is not localized.

FIG. 19 shows assessments of the integrity of the sample when there is an incorrect test setup.

FIG. 27 shows an interface for a test apparatus for performing an integrity test or a leak test.

FIG. 29 shows yet another interface for the apparatus.

DETAILED DESCRIPTION

In the following text, a detailed description of examples will be given with reference to the drawings. It should be understood that various modifications to the examples may be made. In particular, one or more elements of one example may be combined and used in other examples to form new examples.

FIGS. 1 to 4 show graphs of assessments of the integrity of a sample over time taken during performance of an integrity test of the sample. In the graphs, the y-axis shows the rate of diffusion of a sample and the x-axis shows the time in seconds from the start of the test. A first line, including an assessment 101, shows assessments of the integrity of the sample over time. A second line 102, shows the maximum rate of diffusion of the sample. The maximum rate of diffusion of the sample may be specific to the sample. The maximum rate of diffusion of the sample may be specified by a manufacturer of the sample.

The assessments of the integrity of the sample are in milliliters per minute. Further, the integrity test is a diffusion test (also referred to as a forward flow or diffusional flow test). At the beginning of each of the tests, the sample is at room temperature.

In FIGS. 1 to 4, the sample is a filter capsule. The filter capsule includes a filter element and a housing.

Figure 1:
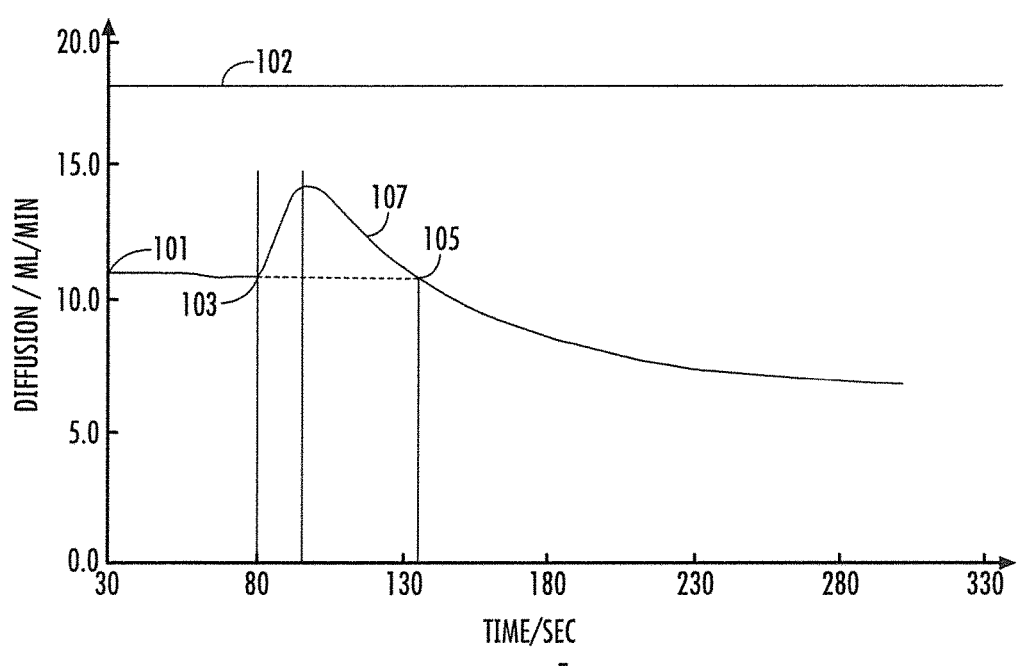
FIG. 1 shows assessments of the integrity of a sample during an integrity test.

FIG. 1 shows assessments of the integrity of a sample over time taken during performance of an integrity test of the sample.

According to the example depicted, the sample is a 10 inch polypropylene filter capsule. During the test, the sample is placed in hot water. During the first 80 seconds of the test, the temperature conditions of the sample housing and filter element are specified temperature conditions (e.g. stable or room temperature). This causes a stable pressure drop per unit of time, which is interpreted by a test apparatus as a stable diffusion rate. Accordingly, during the first 80 seconds of the test, at least one first parameter indicative of at least one of a first volume of the sample, a first temperature of the sample, a first pressure of the sample, and a first assessment of the integrity of the sample may be determined according to the specified temperature conditions. Thus, a first assessment of the integrity of the sample may be the assessment 101, an assessment 103, or an assessment of the integrity of the sample taken before the assessment 103.

The sample is placed in hot water at time t=80 s, after the first assessment of the integrity of the sample, i.e., the assessment 103. After the sample is placed in hot water, the temperature of the sample increases, causing the volume of the sample housing to expand. The temperature increase and volume expansion of the sample housing cause a faster decrease of pressure per unit of time for approximately 15 seconds causing an increased rate of diffusion which determined, e.g., by a testing apparatus (e.g. the testing apparatus 2405 discussed below). The rate of diffusion can be indirectly determined according to an upstream volume of fluid and using Boyle's law. The rate of diffusion can be determined as described in the context of FIG. 37, which describes typical setup of a filter system along with calculation of the rate of diffusion.

The second line 102 shows the maximum rate of diffusion of the sample.

According to the example, there is fluid (e.g. a test gas) in the filter.

Since the sample of the example is a polypropylene filter capsule and polypropylene does not conduct heat efficiently, the rate of heat transfer into the fluid in the capsule is slow.

When heat transfer from the water to the fluid takes place, a pressure drop rate on the upstream side of the filter element (see FIG. 37) is reduced. The testing apparatus may interpret the reduction of the pressure drop rate as a reduction in the diffusion rate (See FIG. 1).

The diffusion rate shown in FIG. 1 and discussed in connection with other figures may be indirectly calculated, e.g. as discussed above. Other methods of indirectly calculating the diffusion rate may also be used.

Between t=80 seconds and t=135 seconds, an assessment of the integrity of the sample is greater than an assessment of the integrity of the sample taken under specified temperature conditions (e.g. at a reference temperature such as room temperature). During the period of 55 seconds between t=80 seconds and t=135 seconds, the deviation from the specified temperature does not have an impact on an indication of the second assessment. In particular, if the test period ends between t=80 seconds and t=135 seconds, and the second assessment of the integrity of the sample is determined in this period, the deviation from the specified temperature caused by immersing the sample in hot water will not have an impact on the indication of the second assessment. The second assessment provides an indication of a passed test or a failed test. In particular, the second assessment indicates whether the integrity test has passed or failed.

After t=80 seconds, a deviation is determined. The deviation is determined based on at least one second parameter indicative of a deviation from the first parameter. In the context of the example, the deviation is determined by detecting a change (i.e. increase) in temperature resulting from immersing the sample in hot water.

An assessment of the integrity of the sample 105 is equal to the assessment 103. The assessment 105 is taken at t=135 seconds. After t=135 seconds, assessments of the integrity of the sample are less than (have a lower value than) the assessments 101 and 103. If the second assessment is taken after the assessment 105, the deviation from the specified temperature conditions will have an impact on the indication of the second assessment. In particular, beyond t=135 seconds, meaning after heating the sample in hot water for 55 seconds, the assessments of the integrity of the sample fall below the assessments 101 and 103, thereby generating a possibility that the indication of the second assessment that the test has been passed is incorrect. Such an incorrect indication of a passed test can put a patient's life at risk. Accordingly, by comparing the first assessment of the integrity of the sample taken before the deviation with the second assessment of the integrity of the sample taken after the deviation, it is possible to determine whether the indication provided by the second assessment is incorrect.

The example of FIG. 1 shows that
if there is a deviation from a first temperature of the sample (i.e. a temperature taken under specified temperature conditions),
the deviation is a temperature increase, and
the increase takes place less than 56 seconds before the second assessment is determined,
there is no negative impact on the indication of the second assessment.

Accordingly, an error message identifying a possibility that the indication of the second assessment is incorrect would not be generated under these conditions.

The sample may be associated with a specified limit value. In the context of FIG. 1, the specified limit value may apply to the filter element of the sample. The specified limit value may be supplied by a manufacturer of the filter element. The specified limit value may be a maximum rate of diffusion of the sample (e.g. a maximum rate of diffusion of the filter element) or a maximum pressure limit of the sample (e.g. a maximum pressure limit of the filter element). The maximum rate of diffusion and maximum pressure limit may be referred to as design characteristics of the sample.

If the second assessment is less than the maximum rate of diffusion of the sample under specified temperature conditions (i.e. before the temperature increase), if the temperature increase takes place and the second assessment is determined in less than (in the present example) 56 seconds, and if the second assessment indicates a failed test, then a possibility that the indication of the second assessment is incorrect may be identified. Further, in view of the identification of the possibility, an incorrect test setup may be detected.

For example, an assessment 107 may be determined as a second assessment of the integrity of the sample. According to the example, the second assessment provides an indication of a failed test in view of the maximum rate of diffusion of the sample. The assessment 107 may be taken at approximately time t=105 seconds. The time t=105 seconds may be referred to as a specified time. A maximum expected change in the assessment of the integrity of the sample under specified temperature conditions may be received. The maximum expected change may have been determined experimentally. In particular, a number of trial integrity tests may be carried out with different samples having different characteristics. The temperature conditions may be kept stable during the trial integrity tests. The maximum expected change may be the greatest change recorded during the trial integrity tests at the specified time, i.e. at t=105 seconds in the present example.

Determining whether the deviation from the first temperature has an impact on the indication of the second assessment further comprises determining whether the second assessment of the integrity of the sample deviates from the first assessment of the integrity of the sample by a quantity greater than the maximum expected change. When the second assessment of the integrity of the sample deviates from the first assessment of the integrity of the sample by a quantity greater than the maximum expected change, a determination may be made that the deviation has an impact on the indication. According to the present example, for the assessment 107, since the assessment 107 deviates from a first assessment of the integrity of the sample, e.g. the assessment 103, it is determined that the deviation has an impact on the indication of a failed test. Accordingly, a possibility may be identified that the failed test indication is incorrect. An error message may be generated warning that the indication of the failed test might be incorrect.

Figure 2:
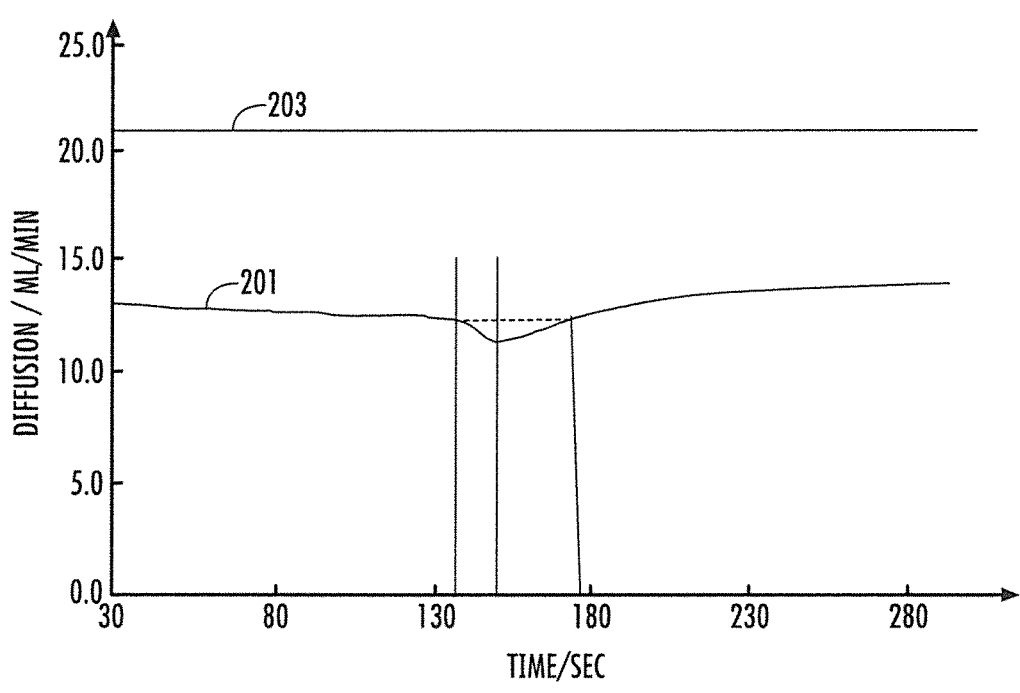
FIG. 2 shows another example of assessments of the integrity of the sample during an integrity test.

FIG. 2 shows another integrity test of a sample. In the example of FIG. 2, the sample is a 10 inch polypropylene filter capsule.

FIG. 2 shows assessments of the integrity of the sample under specified temperature conditions. In the example of FIG. 2, the sample is at room temperature under the specified temperature conditions. During the test, the sample is immersed in cold water.

A line 201 shows assessments of the integrity of the sample over time. A line 203 shows the maximum rate of diffusion of the sample.

During the first 135 seconds of the test, the temperature conditions are specified temperature conditions, e.g., stable. While the temperature conditions are stable, at least one first parameter indicative of at least one of a first volume of the sample, a first temperature of the sample, a first pressure of the sample and a first assessment of the integrity of the sample is determined. In particular, the at least one first parameter may be indicative of the first temperature of the sample.

A line 201 shows assessments of the integrity of the sample over time. A line 203 shows the maximum rate of diffusion of the sample. The maximum rate of diffusion of the sample may be specific to the sample. The maximum rate of diffusion of the sample may be determined by a manufacturer of the sample.

According to the example FIG. 2, a deviation from the first temperature occurs at time t=135 seconds. In this case, the deviation is a temperature decrease brought about by immersing the sample in cold water. When the sample is placed into cold water, the volume of the sample is reduced. The reduction in volume reduces the decrease in pressure over time for approximately 15 seconds. The change in pressure may be used to calculate a rate of diffusion of the sample, e.g. by the testing apparatus. In particular, the testing apparatus may interpret a slower decrease of pressure as a reduction in the rate of diffusion of the sample.

Since the polypropylene of the sample does not conduct heat efficiently, the rate of heat transfer from fluid within the sample to the water outside the sample is slow. The heat transfer from the fluid of the sample to the water may lead to a faster decrease of the pressure of the sample. The faster decrease of the pressure of the sample may be interpreted as an increase of the diffusion rate by the testing apparatus.

Diffusion rates between t=135 seconds and t<178 seconds are below diffusion rates determined before t=135 seconds. In other words, assessments of the integrity of the sample taken after t=135 seconds and before time t=178 seconds are less than the first assessment of the integrity of the sample. t=135 seconds may be understood as 135 seconds after the start of the test and t=178 seconds may be understood as 178 seconds after the start of the test. Other references to time t may be interpreted similarly.

During the 43 second period from 135 seconds after the start of the test and 178 seconds after the start of the test the deviation from the first temperature that occurs at t=135 seconds has a negative impact on an indication of any assessment of the integrity of the sample taken during this period. Accordingly, there is a possibility that the indication of the assessment is incorrect. In particular, an assessment of the integrity of the sample taken during this 43 second period may provide an incorrect indication of a passed test. Such an incorrect indication of a passed test may put a patient at risk. After t=178 seconds, the assessment of the integrity of the sample is the same as the first assessment of the integrity of the sample. Beyond t=180 seconds, assessments of the integrity of the sample are greater (i.e. have a greater value) than the first assessment of the integrity of the sample, thereby also creating a possibility of an incorrect indication of a failed test.

In the example of FIG. 2, if a second assessment of the integrity of the sample is taken less than 43 seconds after the temperature deviation (i.e. temperature decrease) then the temperature deviation has a negative impact on an indication of the second assessment. If the second assessment provides an indication of a passed test, the indication may be incorrect. Further, by evaluating the first assessment of the integrity of the sample and the second assessment of the integrity of the sample in view of a maximum expected change, as described above, a possibility that the second assessment provides an incorrect indication of a passed test can also be identified.

If the first assessment of the integrity of the sample is less than a maximum rate of diffusion of the sample before the temperature deviation, the second assessment occurs after 44 seconds, and if the second assessment provides an indication of a failed test, the maximum expected change associated with the sample can be used to determine that the temperature deviation has an impact on the indication of the failed test, and that the indication of the failed test might be incorrect.

Figure 3:
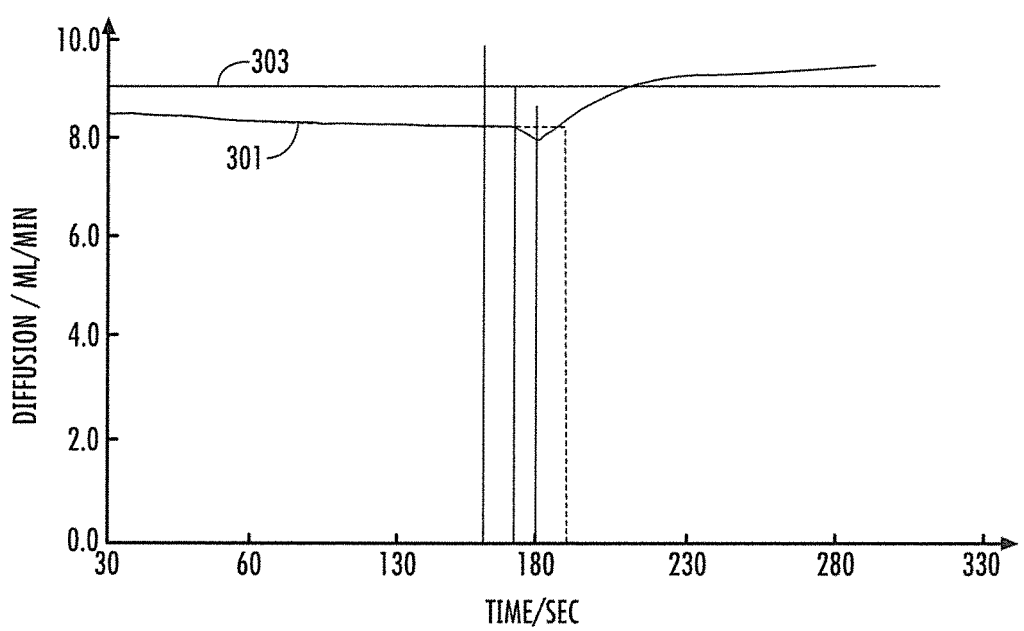
FIG. 3 shows yet another example of assessments of the integrity of the sample during an integrity test.

FIG. 3 shows another example of performing an integrity test of a sample. According to the example, the sample is a size 9 polypropylene filter capsule having walls approximately half as thick as the walls of the filter capsule discussed in connection with FIGS. 1 and 2. The size 9 filter capsule may be 5 inches in length.

From the start of the test to approximately 170 seconds after the start of the test the sample is at the specified temperature conditions. According to the example, the specified temperature conditions are room temperature. At time t=180 seconds, the sample is immersed in cold water, which has about the same temperature as the cold water described in the context of FIG. 2. According to the example, the test is an integrity test. In particular, the test is a diffusion test.

A line 301 shows assessments of the integrity of the sample. A line 303 shows a maximum allowable rate of diffusion of the sample.

When the sample is placed into cold water, the volume of the sample contracts and the temperature of the sample decreases. Accordingly, the decrease in pressure over time slows down, which may be interpreted as a reduction in the rate of diffusion by the testing apparatus. The filter capsule of the example is a 5 inch filter capsule. Further, the filter capsule has a thinner wall than the filter capsule of FIGS. 1 and 2. Accordingly, the volume of the filter capsule contracts for a shorter period of time in comparison to the capsule of FIGS. 1 and 2. In particular, the volume of the filter capsule contracts for ten seconds. In contrast, the volume of the capsule of FIG. 2 contracted for 15 seconds after being immersed in cold water.

Further, heat transfer from the capsule begins (or becomes significant) 10 seconds after the capsule is immersed in the cold water. Because of the thinner wall of the capsule, the change in volume (i.e. contraction) due to heat transfer goes faster in the example of FIG. 3 in comparison to the example of FIG. 2. A fluid (i.e. a gas) is contained within the filter element of the filter capsule.

In comparison to the example of FIG. 2, the heat transfer from the fluid of the filter to the cold water occurs more quickly as indicated by the steeper curve starting at t=180 seconds. When the heat transfer takes place, the decrease in pressure over time occurs more quickly. This may be interpreted by the testing apparatus as an increase in the diffusion rate. In the context of the example, the assessment of the integrity of the sample is a rate of diffusion.

In the context of the example, specified temperature conditions (e.g. stable temperature such as room temperature) prevail from t=0 seconds, i.e. the start of the test, to t=170 seconds. At least one first parameter indicative of at least one of a first volume of the sample, a first temperature of the sample, a first pressure of the sample, and a first assessment of the integrity of the sample may be determined under the specified temperature conditions prevailing from the start of the test to 170 seconds after the start of the test.

According to the example, a deviation from the first parameter occurs at t=170 seconds. The at least one second parameter indicative of the deviation may include temperature. The deviation includes a deviation from the first volume in view of the contraction of the sample that begins at t=170 seconds. In addition, the deviation includes a deviation from the first temperature brought about by the immersion of the sample in the cold water. Further, the deviation includes a deviation from the first assessment as shown by the decrease in the rate of diffusion beginning at t=170 seconds.

A parameter indicative of a second assessment of the integrity of the sample may be determined after t=170 seconds. In other words, at least one third parameter indicative of a second assessment of the integrity of the sample may be determined after the parameter indicative of the deviation is determined. If the at least one third parameter is determined between t=170 seconds and t=190 seconds, the second assessment of the integrity of the sample provides an indication of a passed test. This is because the second assessment of the integrity of the sample corresponds to a rate of diffusion less than the maximum rate of diffusion associated with the sample.

According to the example, the integrity of the sample is assessed as a rate of diffusion. Accordingly, the first assessment of the integrity of the sample is a first rate of diffusion and the second assessment of the integrity of the sample is a second rate of diffusion.

If the second assessment of the integrity of the sample is taken between time t=170 seconds and time t=190 seconds, the deviation has an impact on the indication of the second assessment. This is because the rate of diffusion between 170 seconds and 190 seconds is lower than the first rate of diffusion. Accordingly, a possibility is identified that the indication of the second assessment is incorrect. In particular, a possibility is identified that the indication of the passed test provided by the second assessment is false or incorrect. If the second assessment of the integrity of the sample is taken after t=190 seconds, the deviation is determined to have an impact on the second assessment. In particular, after t=190 seconds, the rate of diffusion of the sample is higher than the rate of diffusion corresponding to the first assessment of the integrity of the sample. Accordingly, a possibility may be identified that the indication of the second assessment is incorrect, i.e. the second assessment provides an incorrect indication of a failed test.

Alternatively, the deviation could be determined to have an impact on the second assessment by determining whether the second assessment deviates from the first assessment by a quantity greater than the maximum expected change associated with the second assessment of the integrity of the sample under specified temperature conditions. The maximum expected change may be obtained for the time when the second assessment of the integrity of the sample is performed and may be specific to (i.e. may correspond to) the characteristics of the sample.

Figure 4:
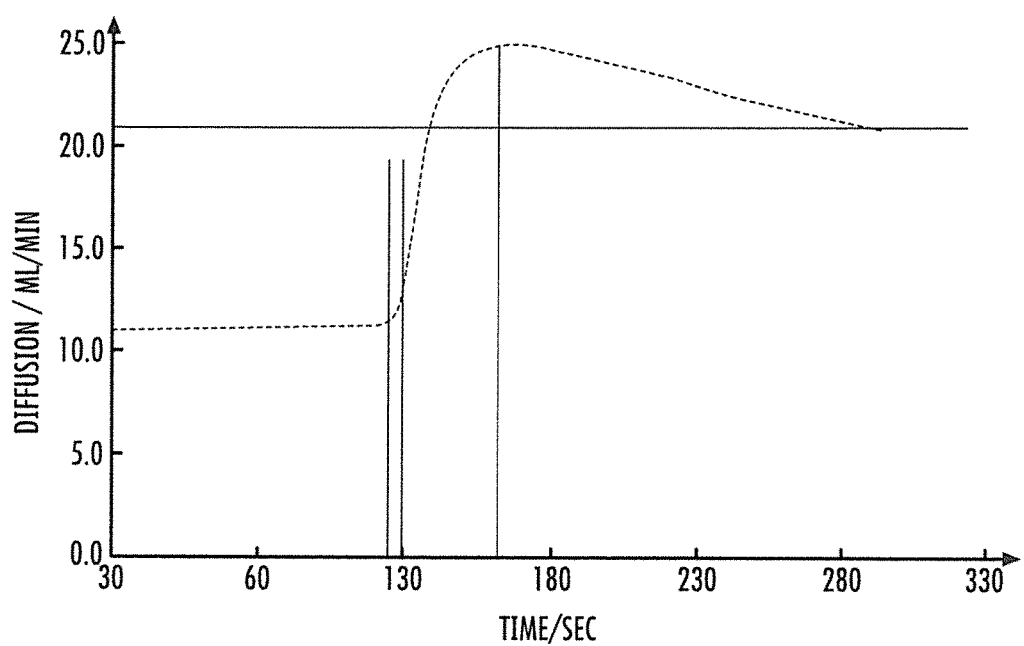
FIG. 4 shows yet another example of assessments of the integrity of the sample during an integrity test.

FIG. 4 shows another example of an integrity test of a sample. In the example of FIG. 4, the sample is a 10 inch stainless steel housing. The integrity test is a diffusion test. From the start of the test to approximately 124 seconds after the start of the test, a specified temperature is maintained. In the example of FIG. 4, the specified temperature is room temperature. At time t=124 s, the sample is immersed in cold water which has about the same temperature as the cold water described in the context of FIGS. 2 and 3. Upon immersion of the sample in cold water, the sample contracts and its volume is reduced for less than 5 seconds. After the period of contraction, there is a rapid transfer of heat from fluid within the sample to the wall of the sample. The rapid transfer of heat occurs for a period of approximately 40 seconds. After the rapid transfer of heat, the rate of heat transfer from the sample slows down due to the low conductivity of the fluid within the sample. In this case, the fluid within the sample is air.

In comparison to the polypropylene filter capsules discussed above, the volume of the stainless steel housing contracts to a much lesser extent. The immersion of the stainless steel housing in cold water has less of an effect on the volume of the stainless steel housing than a similar immersion did on the polypropylene filter capsule because the thermal expansion coefficient of polypropylene is approximately 9 times the thermal expansion coefficient of stainless steel.

Therefore, in contrast to the polypropylene filter capsule discussed in connection with FIGS. 1 to 3, there is no reduction in the rate of diffusion upon cooling of the sample. Instead there is just a short phase of slow increase in the rate of diffusion as the cooling down of the fluid inside the steel housing has a much greater impact on the rate of diffusion than the volume reduction. As in the previous examples, the rate of diffusion corresponds to the assessment of the integrity of the sample. Since the rate of heat transfer for stainless steel is much faster than rate of heat transfer for polypropylene, the fluid inside the stainless steel housing that is close to the wall of the housing is rapidly cooled. The impact on the determined rate of diffusion is reflected in the steep curve shown in FIG. 4. When the air close to the wall of the housing has been cooled down, the rate of heat transfer is slower and the rate of pressure decrease slows down. This may be interpreted by the testing apparatus as a reduction in the rate of diffusion.

FIG. 5 shows thermal expansion coefficients for various materials determined at 25° C. In particular, the great difference between the thermal expansion coefficient of polypropylene and the thermal expansion coefficient of stainless steel can be seen. Accordingly, the thermal expansion coefficient of the sample (along with the material composition of the sample) has an effect on the way the sample reacts to deviations such as changes in temperature.

Figure 6:
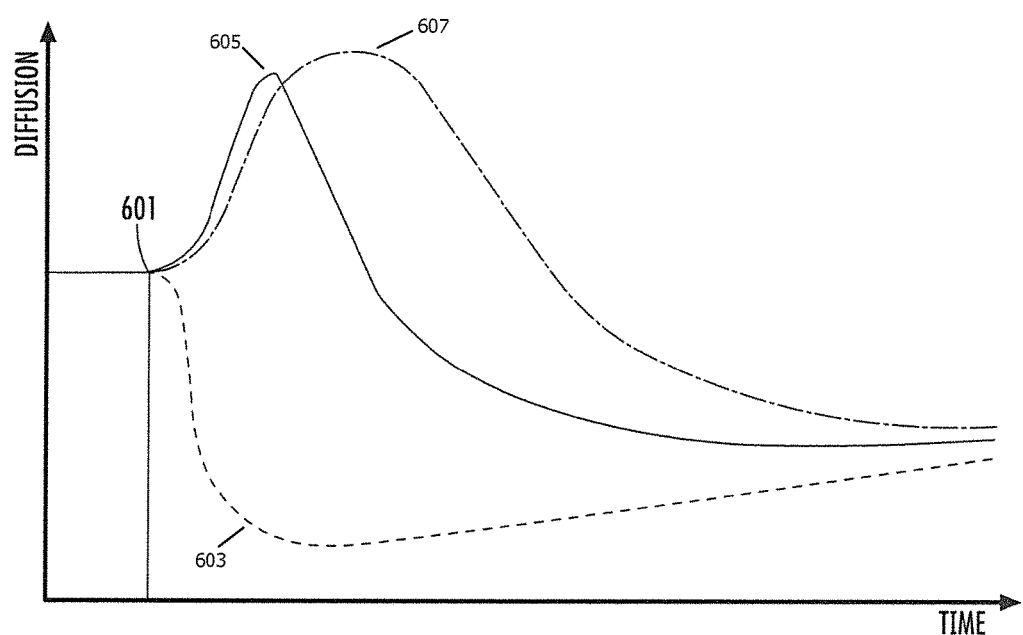
FIG. 6 compares integrity test assessments for different samples after a temperature decrease.
Figure 7:
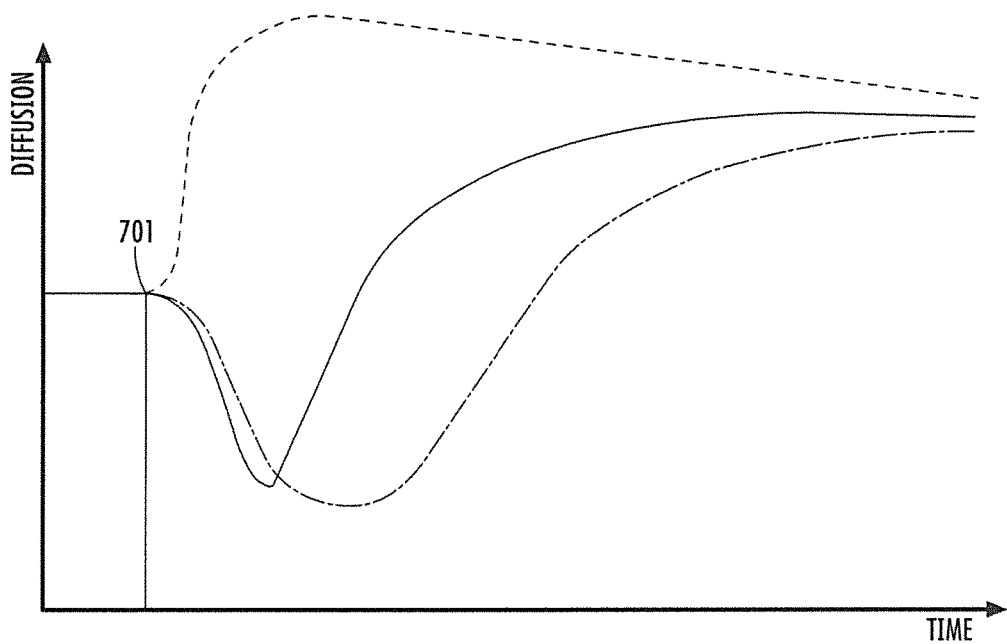
FIG. 7 compares integrity test assessments for different samples after a temperature decrease.

FIGS. 6 and 7 compare results shown in FIGS. 1 to 4.

FIG. 6 shows differing responses to deviations (e.g. resulting from changing environmental conditions, such as changing temperature) for samples having different design characteristics.

In the example of FIG. 6, a rate of diffusion is plotted on the y-axis and time is plotted on the x-axis. A temperature deviation occurs at a point 601, a certain number of seconds from the start of the test. In the example of FIG. 6, the deviation is a temperature increase. The integrity of the samples whose behavior is depicted in FIG. 6 is assessed using the rate of diffusion of the corresponding sample. Accordingly, a first assessment of the integrity of the stainless steel housing sample could be the rate of diffusion corresponding to the point 601. For the stainless steel housing, a temperature increase causes a sharp and rapid decrease in the rate of diffusion, which continues until point 603. In contrast, the thin walled polypropylene filter capsule shows a sharp increase in the rate of diffusion following the temperature increase, which peaks at point 605. The sharp increase is followed by a rapid decrease that gradually levels off, forming a sharp peak.

The thick walled polypropylene capsule also shows an increase in the rate of diffusion in response to the temperature increase. However, in contrast to the thin walled polypropylene filter capsule, the rate of diffusion remains high for much longer for the thick walled polypropylene capsule before beginning to decline more gradually at point 607. Accordingly, the curve corresponding to the thick walled polypropylene filter capsule (including point 607) forms a broader more rounded peak in contrast to the curve corresponding to the thin walled polypropylene capsule (including point 605).

FIG. 7 is similar to FIG. 6 except that the effect of a temperature decrease, which occurs at a point 701, on the rate of diffusion is shown for samples having different design characteristics. Similar to FIG. 6, the y-axis of the graph of FIG. 7 shows a rate of diffusion and the x-axis shows the time in seconds. Further, the rate of diffusion functions as an assessment of the integrity of the samples. After the temperature decrease, the rate of diffusion of the stainless steel housing rapidly increases before gradually decreasing. In contrast, the polypropylene capsules show a decrease in the rate of diffusion in response to the temperature decrease. The decrease in the rate of diffusion is followed by an increase in the rate of diffusion. The graph of FIG. 6 is basically the mirror image of the graph of FIG. 7.

Figure 8:
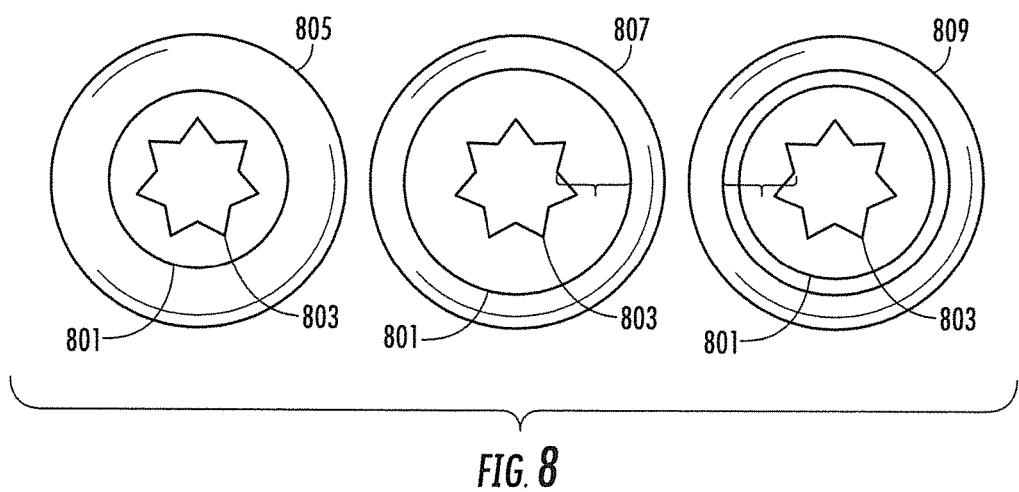
FIG. 8 shows volume and temperature deviations of a sample due to temperature changes in an environment of the sample.

FIG. 8 shows effects of a deviation (e.g. resulting from changing environmental conditions, such as changing temperature) on a sample. In the example of FIG. 8, the sample is a filter capsule 801 including a filter element 803. Before being placed into hot water at time $t_0$ (some time after the start of the test in this case), the filter capsule 801 may be at a specified temperature, i.e. room temperature. At time $t_0$, the filter capsule 801 is placed into a container of hot water 805. The filter capsule 801 may be fully immersed. A container of hot water 807 shows the filter capsule 801 at time $t_1$ (which occurs after $t_0$). At time $t_1$, the filter capsule has expanded in view of the deviation from the specified temperature resulting from the placement of the filter capsule in the container of hot water 805. The shading near the wall of the filter capsule 801 represents horizontal temperature gradients resulting from an increase in temperature inside the filter capsule 801. A container of hot water 809 shows the filter capsule 801 after additional heat transfer at time $t_2$.

Further, darkness near the wall of the filter capsule 801 reflects increased temperature inside the filter capsule 801. The hot water containers 805, 807, and 809 are the same hot water container at different times. The hot water container 807 and the hot water container 809 show horizontal temperature gradients as shading near the wall of the filter capsule 801.

The frame of reference of the present application is the earth. Accordingly, horizontal and vertical may be understood with respect to the surface of the earth.

Figure 9:
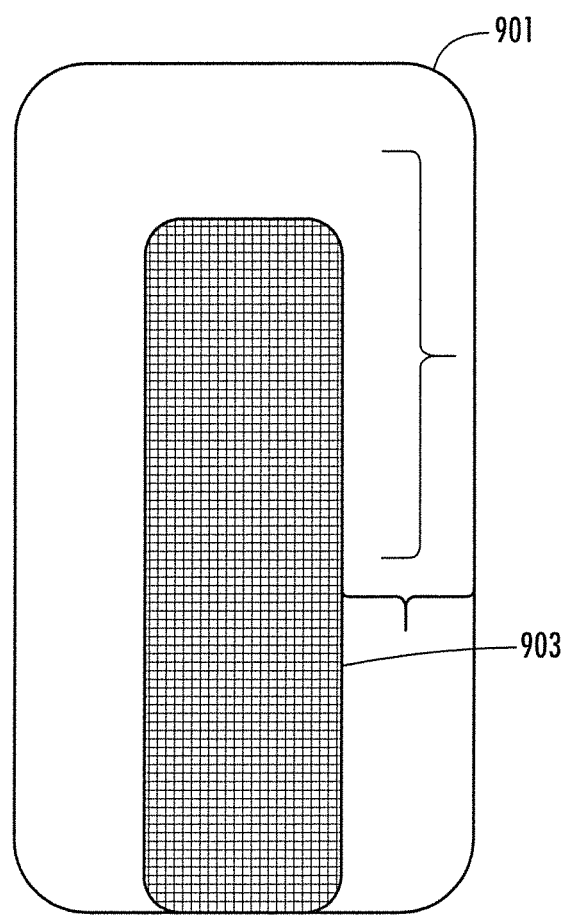
FIG. 9 shows temperature gradients inside the sample resulting from a temperature change outside the sample.
Figure 10:
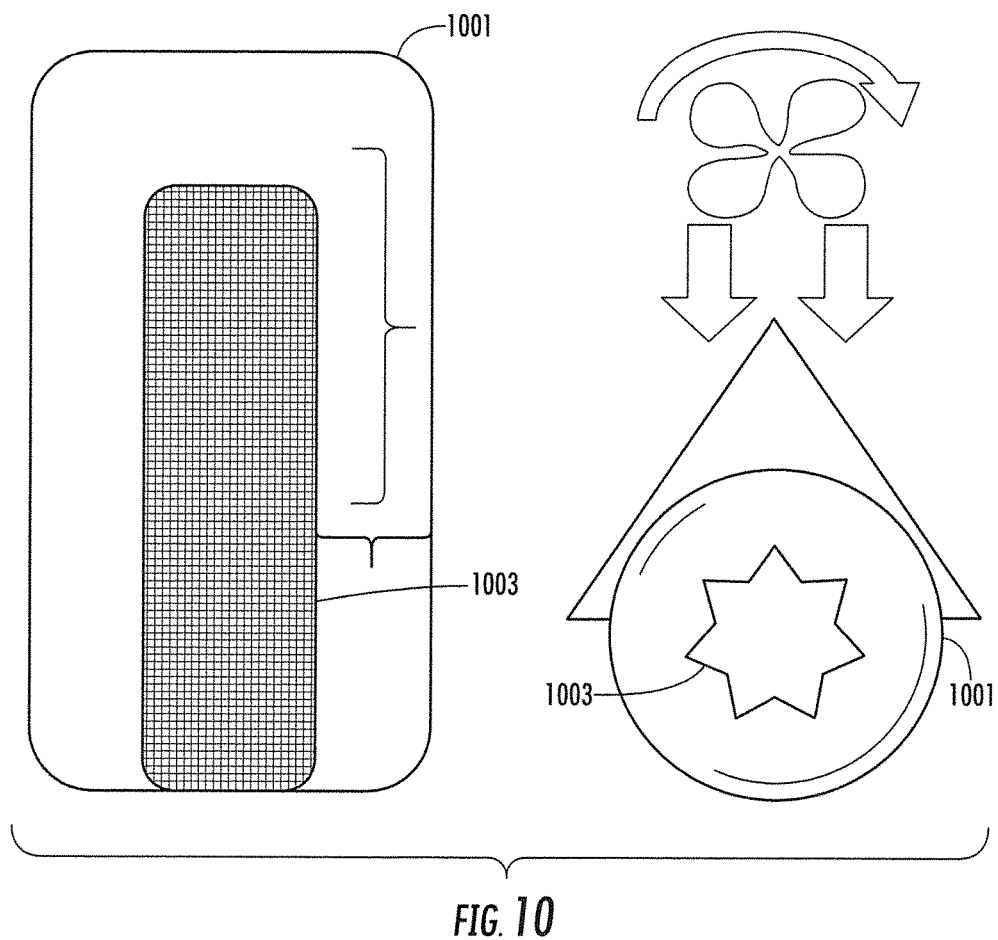
FIG. 10 shows effects on the sample of a localized temperature deviation in the environment of the sample.

FIG. 9 shows another example of the effects of a deviation from a specified temperature on a sample. In the example, the sample is a filter capsule 901 including a filter element 903. The temperature gradients depicted in FIGS. 8 and 9 may occur in view of the poor heat conductivity of fluid inside the filter capsule 801 and the filter capsule 901. Further, the lower density of hot air inside the filter capsule 901 causes the hot air to rise inside the filter capsule, thus creating vertical temperature gradients. The vertical temperature gradients are shown in FIG. 9 as darkness at the top of the filter capsule 901 gradually becoming lighter towards the bottom of the filter capsule 901. FIG. 10 shows an example of an effect of a localized temperature deviation from a specified temperature of the sample. The localized deviation may be caused by a heat fan. The sample is depicted as a filter capsule 1001 including a filter element 1003. The sample is depicted from different perspectives in order to show vertical and/or horizontal temperature gradients. High temperatures are represented by darkened portions whereas relatively lower temperatures are represented by lighter portions within the filter capsule 1001.

Accordingly, if a temperature deviation comes from only one side of the sample (i.e. filter capsule 1001), the impact on the test will be different in comparison to a situation in which a temperature deviation occurs on all sides of the sample at the same time. Localization of the deviation in temperature may impact the rate of heat transfer to the sample. In addition, localization of the deviation from the specified temperature may impact the way the volume of the sample changes during the course of the test. In particular, the sample will expand in an uneven way.

Figure 11:
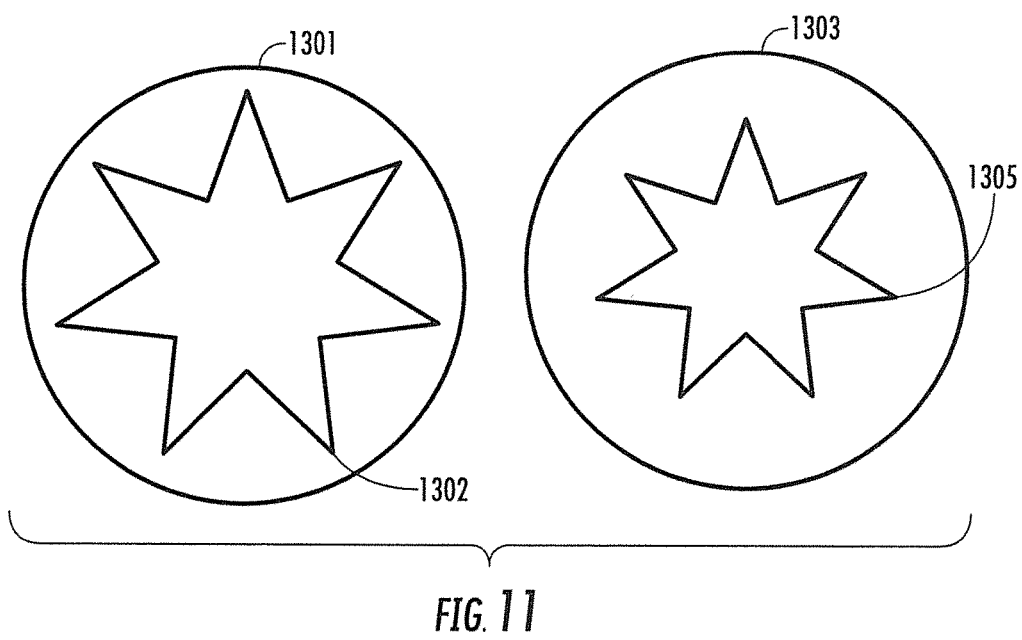
FIG. 11 shows two different types of filter, each having a different intermediate volume.

FIG. 11 shows samples with different intermediate volumes. In the example of FIG. 11, each sample is a filter including a filter element. The intermediate volume of the filter refers to the space between the filter element and an inner wall of the filter (i.e. a housing of the filter). The intermediate volume may also be referred to as the net volume. A small distance capsule may have a relatively small amount of space between the filter element and an inner wall of the filter. A large distance capsule may have a relatively large amount of space between the filter element and an inner wall of the filter. Accordingly, a filter 1301 has a relatively small amount of space between an inner wall of the filter 1301 and a filter element 1302. Hence, the filter 1301 has a relatively small intermediate volume.

A filter 1303 has a larger intermediate volume than the filter 1301. In particular, there is more space between a filter element 1305 and an inner wall of the filter 1303 in comparison to the amount of space between the filter element 1302 and the inner wall of the filter 1301.

Figure 12:
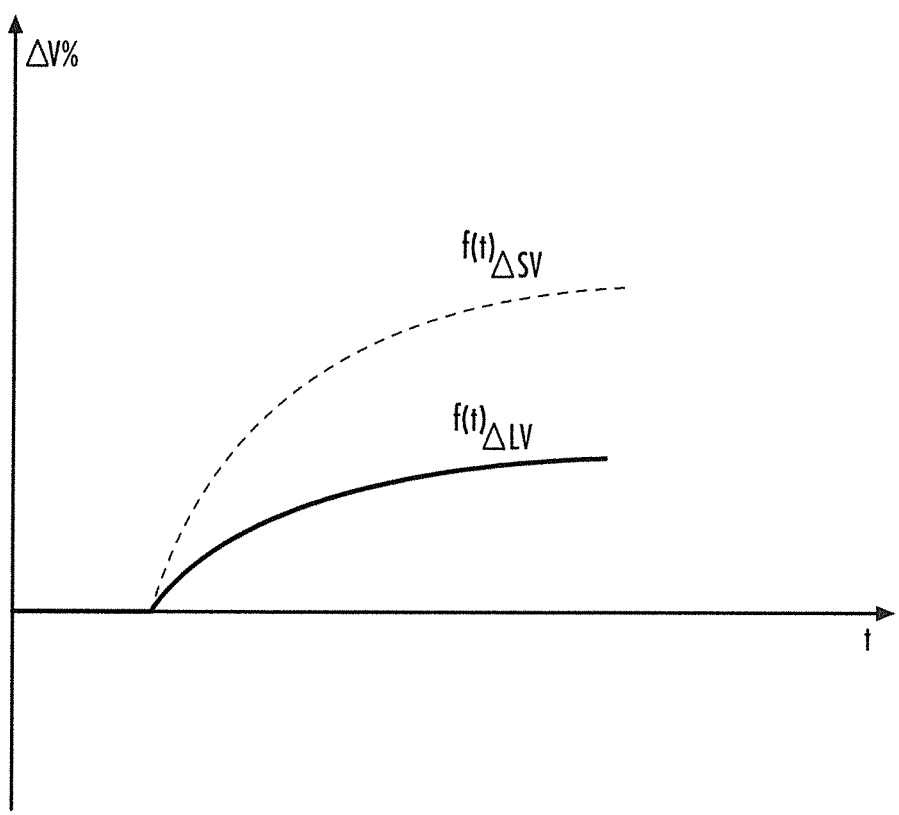
FIG. 12 shows volume deviations in response to a temperature increase in view of the filter type.

FIG. 12 shows the impact of a temperature increase on filters having different intermediate volumes. The y-axis of the graph depicted in FIG. 12 shows a percentage change in volume while the x-axis shows time in seconds. The temperature increase may be relative to a specified temperature, e.g. room temperature. As can be seen from FIG. 12, a temperature increase has a greater impact on a filter capsule with a smaller intermediate volume than it does on a filter capsule with a larger intermediate volume. With reference to FIG. 11, if all other factors remain stable, a temperature increase will have a greater impact on the filter capsule 1301 than it will on the filter capsule 1303. In particular, because the temperature increase causes a greater deviation in the volume of the filter capsule 1301 then it causes in the volume of the filter capsule 1303, this may result in a greater effect on the rate of diffusion of the filter capsule 1301 and the corresponding assessment of the integrity of the filter capsule 1301 in comparison to the filter capsule 1303.

FIG. 12 may be understood to represent the time dependent function for volume change for each filter capsule depicted in FIG. 11 in response to a temperature increase. Both the filter capsule 1301 and the filter capsule 1303 have the same dimensions. The filter capsules also have the same material composition.

FIG. 14 shows values determined from a sample exposed to a heating fan during a test. According to the example, the sample is a filter capsule and the test is an integrity test of the filter capsule. A first column 1701 shows the time in seconds as measured from the start of the test. A second column 1703 shows temperature values determined via a sensor on a wall of the sample facing the heating fan. A third column 1705 shows rates of diffusion corresponding to the times and temperatures. The ambient temperature, e.g. the room temperature, is 22.29° C. The temperature values in the column 1703 are in ° C., the values in the column 1705 are in milliliters per minute (ml/min).

According to the example, the heating fan generated a progressive temperature increase from the side facing the heating fan. The relative air humidity was between 40% and 60%.

In order to obtain comprehensive empirical data, it may be advisable to conduct trials with several sensors in and or around the sample.

Figure 15:
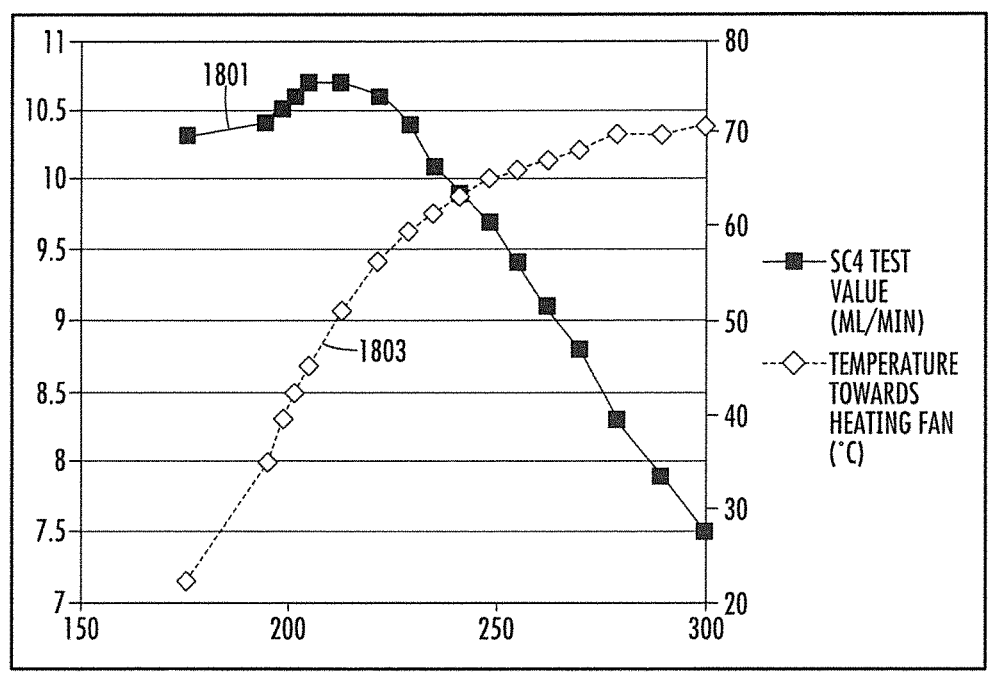
FIG. 15 also shows integrity assessments of the sample resulting from localized temperature deviation.

FIG. 15 shows a graph of the values depicted in FIG. 14. The x-axis shows the time in seconds, the y-axis on the left side of the graph shows rates of diffusion in milliliters per minute and the y-axis on the right side of the graph shows the temperature determined by the sensor facing the heating fan in ° C. A line 1801 tracks rate of diffusion values, i.e. SC4 test values. A line 1803 tracks temperature values determined via the temperature sensor facing the heating fan.

FIG. 16 shows another example of data generated during integrity test of a sample. In this case, the integrity test is a diffusion test and the sample is a filter capsule. According to the example, the sample was immersed in warm water, which was about 34° C. A first column 1901 shows the time in seconds from the start of the test. A second column 1903 shows the temperature of the water surrounding the sample. A third column 1905 shows rates of diffusion corresponding to the times and temperatures. The rates of diffusion may be in milliliters per minute and may be referred to as SC4 test values. Once the sample was placed in the water, the temperature increase around the sample was instant and homogenous all around the sample wall. The humidity was 100%. The ambient temperature around the sample before the sample was placed in the water was 22.30° C.

Figure 17:
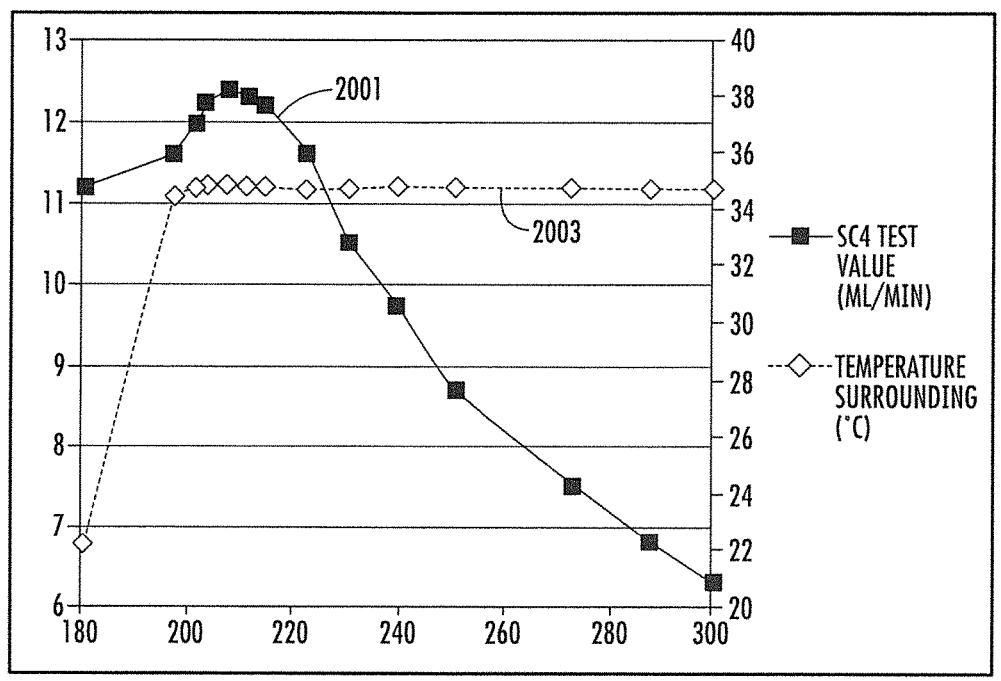
FIG. 17 also shows sample integrity assessments after a temperature deviation that is not localized.

FIG. 17 shows a graph of the data depicted in FIG. 16. The x-axis shows the time in seconds, the y-axis in the left side of the graph shows the rate of diffusion, and the y-axis on the right side of the graph shows the temperature of the water in ° C. A line 2001 shows the rates of diffusion recorded during the test. A line 2003 shows the temperature of the water surrounding the sample in ° C., as recorded during the test.

The examples of FIGS. 14 to 17 show that it may be an advantage to determine localization of deviations from a specified temperature of the sample. In addition, the examples of FIGS. 14 to 17 show that it may be an advantage to measure humidity. The impact of immersing a sample and causing an increase in temperature from 22.3° C. to 34.9° C. at 100% humidity is much greater than the impact of causing a localized increase in temperature from 22.3° C. to 70.8° C. via a heating fan. This greater impact is depicted in FIGS. 14 to 17.

The examples discussed above show that the impact from temperature changes on a sample is complex. Deviations from a first temperature of the sample may cause a corresponding deviation from a first volume of the sample. Further, temperature changes may involves temperature gradients, i.e. different temperatures in different parts of the sample. Due to the volume deviation brought about by the temperature deviation, assessments of the integrity of the sample cannot simply be corrected using the ideal gas law. Therefore, the computer-implemented method as discussed in the present application improves the reliability of an integrity or a leak test of a sample.

Accordingly, aspects disclosed in the present application may provide a scientific and sound approach to using a plurality of sensors in conjunction with a computer implemented method, along with results of empirical studies of samples having various characteristics, to improve test reliability. The sensors may include at least one temperature sensor and/or at least one humidity sensor. The sensors may include a tension sensor and/or a pressure sensor. The empirical studies may account for thermal expansion factors of samples, heat capacity of samples, thermal inertia of different materials, and design characteristics of the samples.

Figure 13:
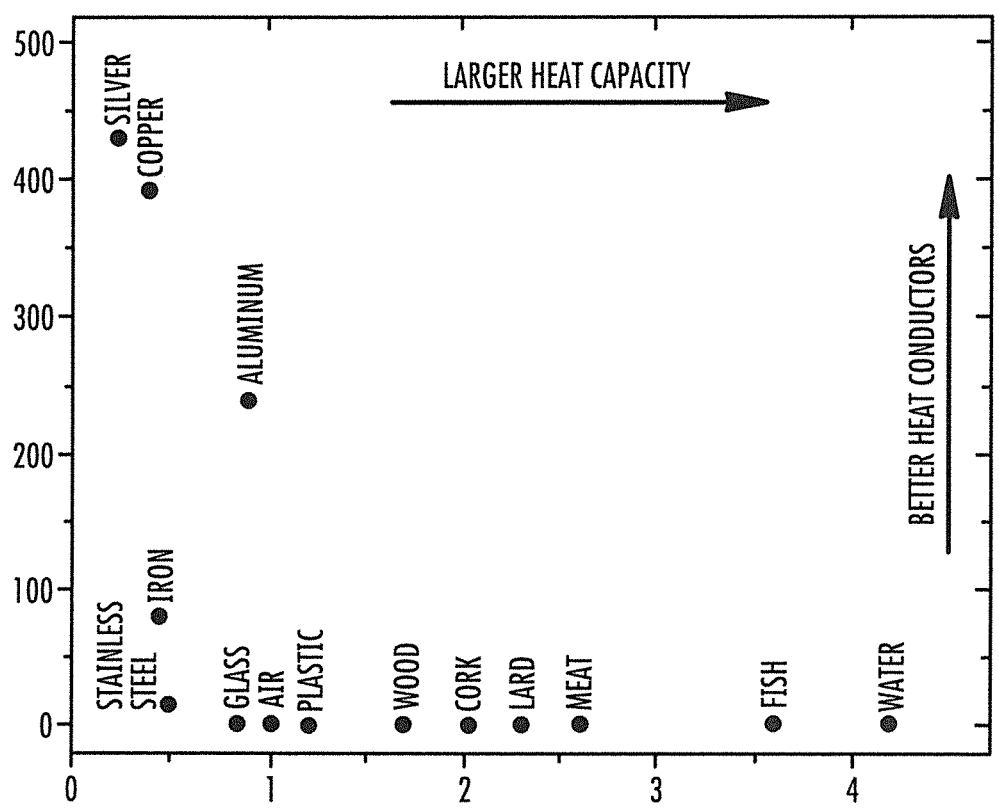
FIG. 13 shows information about heat capacity and conductivity for various materials.

FIG. 13 shows information about heat capacity and conductivity of various materials. Heat capacity is expressed in Joules per unit of weight.

As discussed above, when a possibility is identified that the indication of the second assessment is incorrect, an error message may be generated. In order to determine whether a deviation from the first volume, the first temperature, or the first assessment has an impact on an indication of an assessment of the integrity of a sample being tested, time dependent functions may be used. The time dependent functions may be evaluated throughout the test.

Further, at least one third parameter indicative of a second assessment of the integrity of the sample may be determined after a second parameter indicative of the deviation is determined.

In particular, $f(t)_{\Delta vol}$ is a time dependent function for volume change due to temperature change expressed as a rate of diffusion. For example, the rate of diffusion may be expressed in milliliters per minute. An increase of the volume due to temperature increase results in a positive value.

$f(t)_{\Delta heat}$ is a time dependent function for the heat transfer to a sample expressed as a rate of diffusion. For example, the rate of diffusion may be expressed in milliliters per minute. An increase in temperature results in a negative value.

If there is a temperature deviation and if $f(t)_{\Delta vol} + f(t)_{\Delta heat} \geq 0$ when the second assessment of the integrity of the sample is determined, and if the second assessment is less than the maximum allowable rate of diffusion associated with the sample, it is determined that the deviation does not have an impact on the indication of the second assessment. A possibility then is identified that the second assessment correctly indicates a passed test.

If there is a temperature deviation and if $f(t)_{\Delta vol} + f(t)_{\Delta heat} < 0$ when the second assessment of the integrity of the sample is taken, and if the second assessment is less than the maximum allowable rate of diffusion associated with the sample, then the deviation is determined to have an impact on the indication of the second assessment. In particular, a possibility is identified that the second assessment incorrectly indicates a passed test.

If there is a temperature deviation and if $f(t)_{\Delta vol} + f(t)_{\Delta heat} > 0$ and if the second assessment of the integrity of the sample is greater than the maximum allowable rate of diffusion associated with the sample, then it is determined that the deviation has an impact on the indication of the second assessment and a possibility that the indication of the second assessment incorrectly indicates a failed test is identified.

The identification of a possibility that the indication of the second assessment is incorrect may result in the generation of an error or warning message. In addition or alternatively, the second assessment of the integrity of the sample may be corrected based on empirical data associated with the sample.

By establishing reference situations having various humidity conditions and temperature increases and tracking the behavior of samples over time in each of these situations, it may be possible to correct for the impact of deviations on indications of a passed test or a failed test provided by assessments of the integrity of the corresponding samples. For example, when an assessment of the integrity of the sample corresponds to a rate of diffusion, the rate of diffusion may be corrected during a test in real time or at the end of the test. In particular, empirical data (e.g. collected and/organized in a database) may be used to correct indications of integrity assessments.

Figure 18:
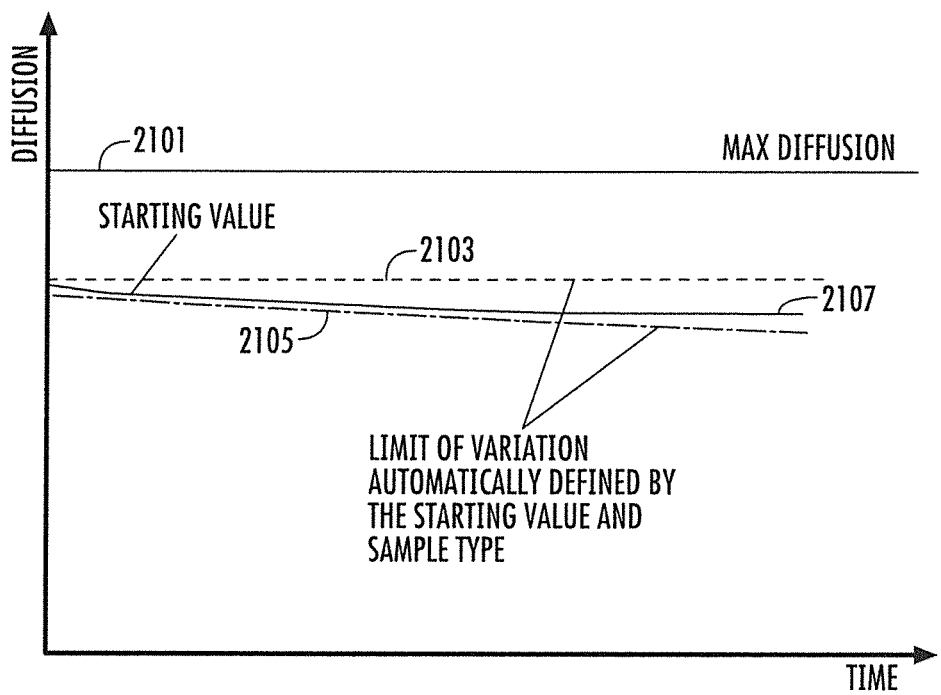
FIG. 18 shows assessments of the integrity of the sample under specified temperature conditions.

FIG. 18 shows evaluation of a maximum change in the assessment of the integrity of a sample under specified temperature (e.g. stable) conditions. The evaluation may be carried out based on standards specific to characteristics of the sample. Temperature conditions of the evaluation may be corrected such that stable conditions can be obtained. In the graph of FIG. 18, the x-axis shows time in seconds and the y-axis shows a rate of diffusion in milliliters per minute. A line 2101 shows the maximum rate of diffusion specific to the sample. A dashed line 2103 shows an upper limit of variation from the starting rate of diffusion and a dashed line 2105 shows a lower limit of variation from the starting rate of diffusion. A solid line 2107 shows the rate of diffusion for the sample recorded over time during a diffusion test. As can be seen from this figure, a certain amount of change in the assessment of integrity under the sample is expected under specified temperature conditions. Such variation will occur even if the temperature is stable throughout the integrity test and even if the setup for the integrity test is correct. When a second assessment of the integrity of the sample deviates from a first assessment of the integrity of the sample by a quantity greater than the maximum expected change, e.g. as determined experimentally, this may be an indication that the integrity test has been setup incorrectly.

FIG. 19 shows values determined or calculated during an integrity test in which the setup of the test is incorrect. The values are plotted in FIG. 20. A correct setup may be understood in view of the discussion of FIG. 37 below.

An example of an incorrect setup for an integrity test may include a closed downstream valve. When the downstream valve is closed, differential pressure across a filter capsule being tested will be reduced due to increased downstream pressure. The rate of diffusion recorded over time will be reduced accordingly. According to the example, the rate of diffusion corresponds to an assessment of the integrity of the sample. According to the example, the sample is a filter capsule. Since the rate of diffusion is directly proportional to the applied differential pressure, a simulation can be carried out based on the starting pressure, the diffusion rate, and the downstream volume.

To determine the maximum expected change in the assessment of the integrity of the sample under specified (e.g. stable) temperature conditions, specific time dependent functions may be used, as described below. For two samples having different characteristics, the time dependent functions may produce different values. For two samples having the same characteristics, the time dependent functions may produce the same values.

A time dependent function $f(t)_{\Delta +max}$ may be used as a specific time dependent function for maximum increase in the assessment of the integrity of the sample under specified temperature conditions, e.g. stable temperature conditions. Specified temperature conditions may be conditions that are stable without correction, or temperature conditions that have been corrected so that they are relatively constant. The function may provide values specifying a rate of diffusion, e.g. in milliliters per minute, in comparison to the initial rate of diffusion at time t=0 seconds, i.e. the start of the integrity test. The function may be used to plot the values of the dashed line 2103 in FIG. 18.

A further time dependent function $f(t)_{\Delta-max}$ may be used to determine a maximum expected decrease in the assessment of the integrity of the sample under specified temperature conditions. As mentioned above, these specified temperature conditions may be temperature conditions that are corrected so that they are relatively steady or constant. The function may provide a value for the rate of diffusion, e.g. in milliliters per minute, in comparison to an initial value of the rate of diffusion at time t=0 seconds, i.e. at the start of the integrity test. The function may be used to determine values on the dashed line 2105 of FIG. 18.

The determined rate of diffusion at time t during an integrity test may be referred to as $Diff_t$. The determined rate of diffusion at the start of the integrity test (or at a time when temperature conditions are stable) may be referred to as $Diff_{t0}$.

If $Diff_t > Diff_{t0} + f(t)_{\Delta+max}$, a rate of diffusion determined during the test differs from a rate of diffusion determined at the start of the test by more than the expected maximum increase in the rate of diffusion under specified temperature conditions.

If $Diff_t < Diff_{t0} - f(t)_{\Delta-max}$, a rate of diffusion determined during the test differs from a rate of diffusion determined at the start of the test by more than the expected maximum decrease in the rate of diffusion under specified temperature conditions.

If either of the functions above evaluates to TRUE, a deviation from one or more of the first volume of the sample, the first temperature of the sample, the first assessment of the integrity of the sample, had an impact on a second assessment of the integrity of the sample taken after the deviation. Further, the second assessment of the integrity of the sample deviates from the first assessment of the integrity of the sample by a quantity greater than the maximum expected change. Accordingly, an error message may be generated, e.g. indicating that the integrity test has been setup incorrectly.

Figure 20:
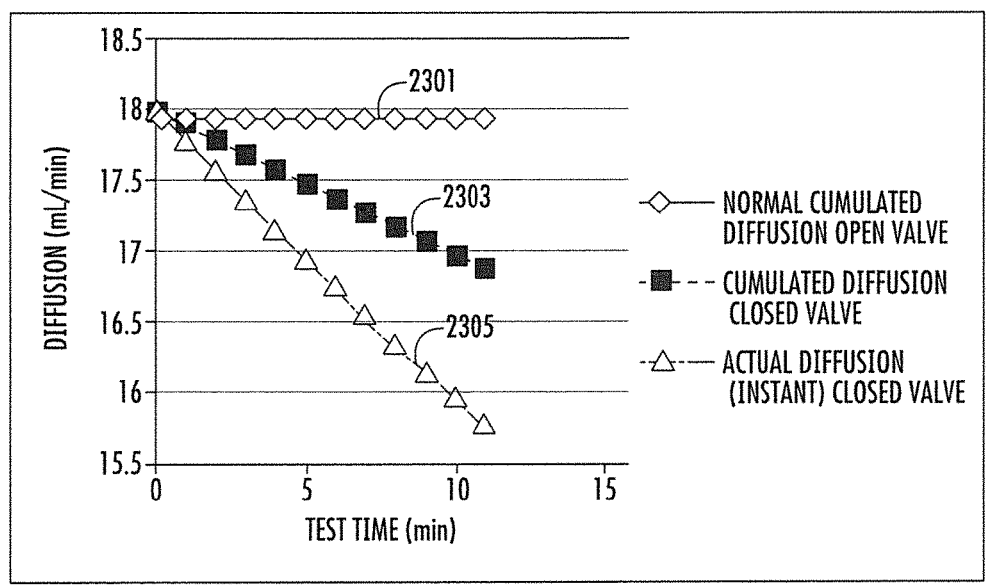
FIG. 20 compares assessments of integrity of the sample when there is a correct test setup with assessments of the integrity of the sample when there is an incorrect test setup.

FIG. 20 shows rate of diffusion values determined over time during an integrity test in various situations. A first line 2301 shows the accumulated average rate of diffusion over time during an integrity test with a correct test setup. The accumulated average rate of diffusion should be understood as the average rate of diffusion measured since the start of the test. A second line 2303 shows the accumulated average rate of diffusion over time for an integrity test with an incorrect setup, i.e. the downstream valve is closed. A third line 2305 shows the instant rate of diffusion for an integrity test with incorrect setup, i.e. the downstream valve is closed. In contrast to the accumulated average rate of diffusion, the instant rate of diffusion is measured with respect to a specific point in time, without regard to the influence of any other point in time.

FIGS. 21 to 26 show different configurations of a computer system for improving the reliability of an integrity test or leak test of a sample. Temperature and/or humidity sensors may be attached or arranged around the sample being tested before starting the test. In addition or alternatively, temperature and/or humidity sensors may be arranged inside the sample. The temperature and/or humidity sensors arranged inside the sample may be directly integrated into the sample, e.g. during the manufacture of the sample. Tension and/or pressure sensors may also be attached or arranged around the sample.

The sensors may be arranged in a number of ways. In particular, non-particle generating magnetic stripes may be used. In addition or alternatively, a jacket with integrated sensors may be used. Also, sensors may be directly integrated on the outside of the sample wall. Further, sensors may be arranged inside the sample. Sensors may be embedded in the wall of the sample.

Figure 21:
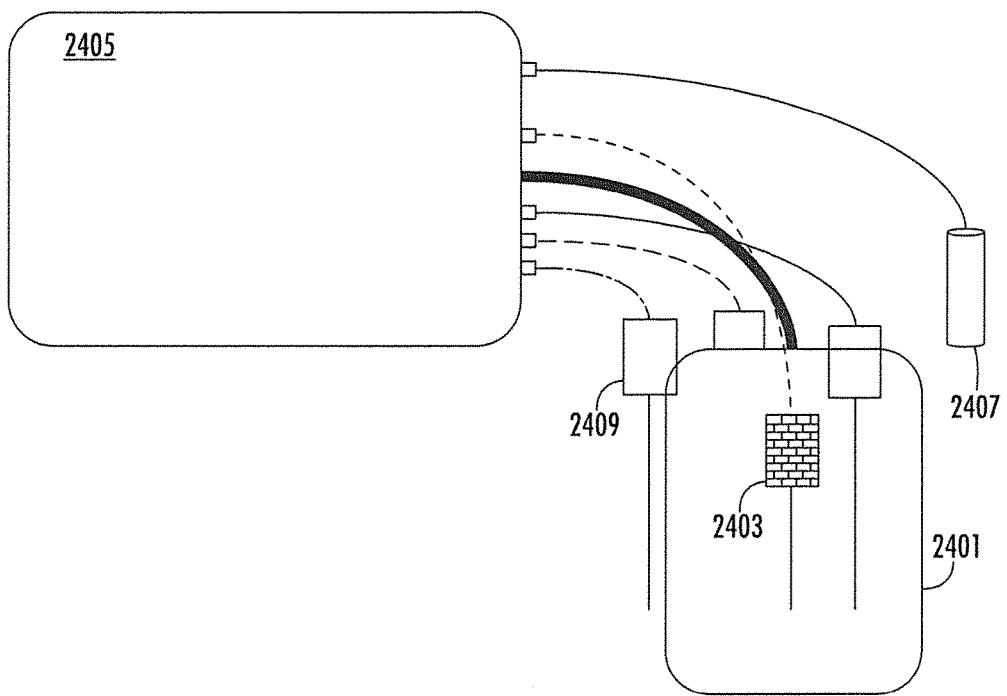
FIG. 21 shows a test setup for an integrity test.

FIG. 21 shows a configuration of the computer system for improving the reliability of an integrity test or leak test of a sample 2401. At least one temperature sensor 2403 may be arranged inside the sample. The sample may be connected to a test apparatus 2405. The sample 2401 may be connected to the test apparatus 2405 via a cable or wireless connection. The sample 2401 may be fluidly connected to the test apparatus 2405. At least one humidity sensor 2407 may be placed outside the sample. The humidity sensor 2407 may be connected to the test apparatus 2405 via a cable or wireless connection. A pneumatic tube may connect the sample 2401 to the test apparatus 2405. At least one external temperature sensor 2409 may be arranged outside the sample. The external temperature sensor 2409 may be connected to the test apparatus 2405 via a cable or wireless connection.

Figure 22:
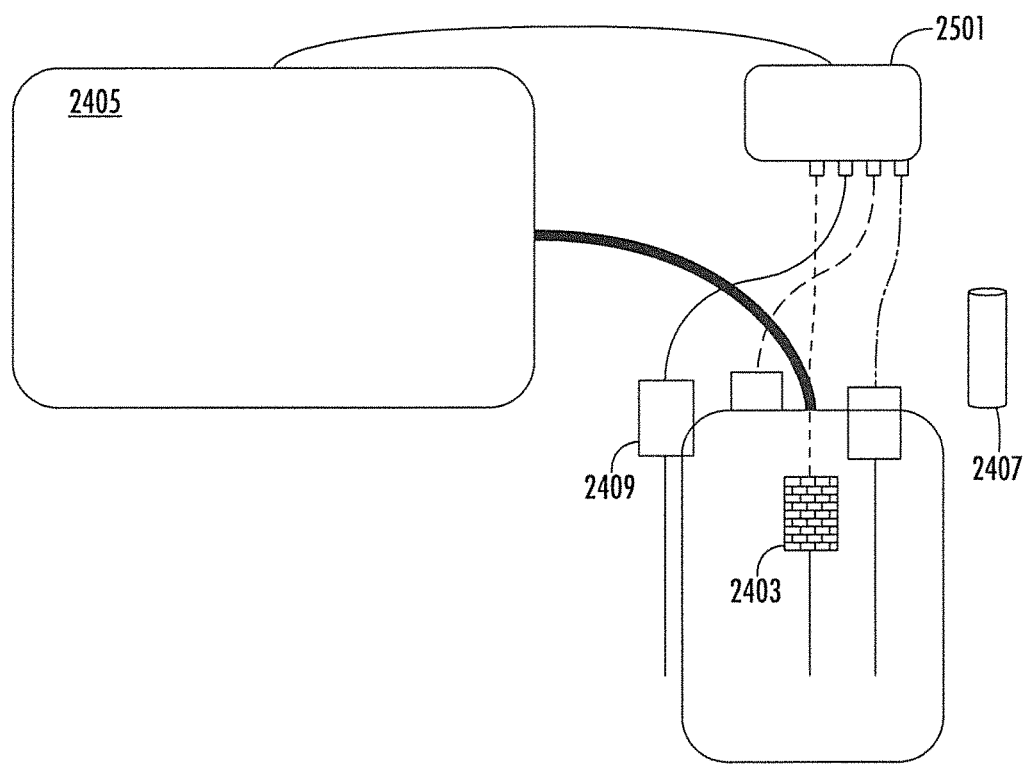
FIG. 22 shows another test setup for an integrity test.

FIG. 22 shows another configuration of the computer system for improving the reliability of an integrity test or leak test of a sample. The configuration of FIG. 22 is similar to the configuration of FIG. 21. In addition, the configuration of FIG. 22 includes an external device 2501. The external device 2501 may be connected to the test apparatus 2405. The external device 2501 may also be connected to the humidity sensor 2407, the external temperature sensor 2409, and the internal temperature sensor 2403. The external system 2501 may carry out one or more steps of the method for improving the reliability of an integrity or leak test of a sample, as discussed above.

Figure 23:
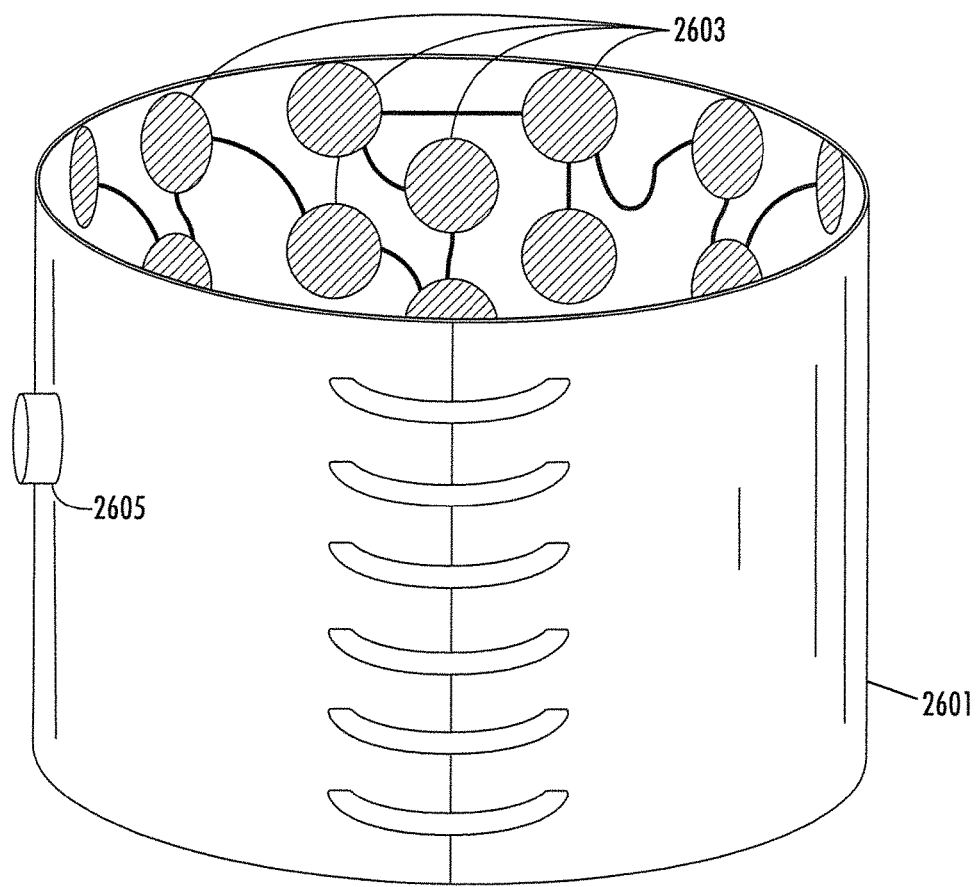
FIG. 23 shows yet another test setup for an integrity test.

FIG. 23 shows another configuration of the computer system for improving the reliability of an integrity test or leak test of a sample. In the configuration of FIG. 23, a sample 2601 may include temperature sensors 2603 inside a jacket of the sample 2601. The temperature sensors 2603 are in direct contact with the wall of the sample 2601. Also depicted is a contact 2605 for connection to a test apparatus via cable or wireless connection. The test apparatus may be the test apparatus 2405 or a similar test apparatus. Also depicted is a closing mechanism of the jacket of the sample 2601.

Figure 24:
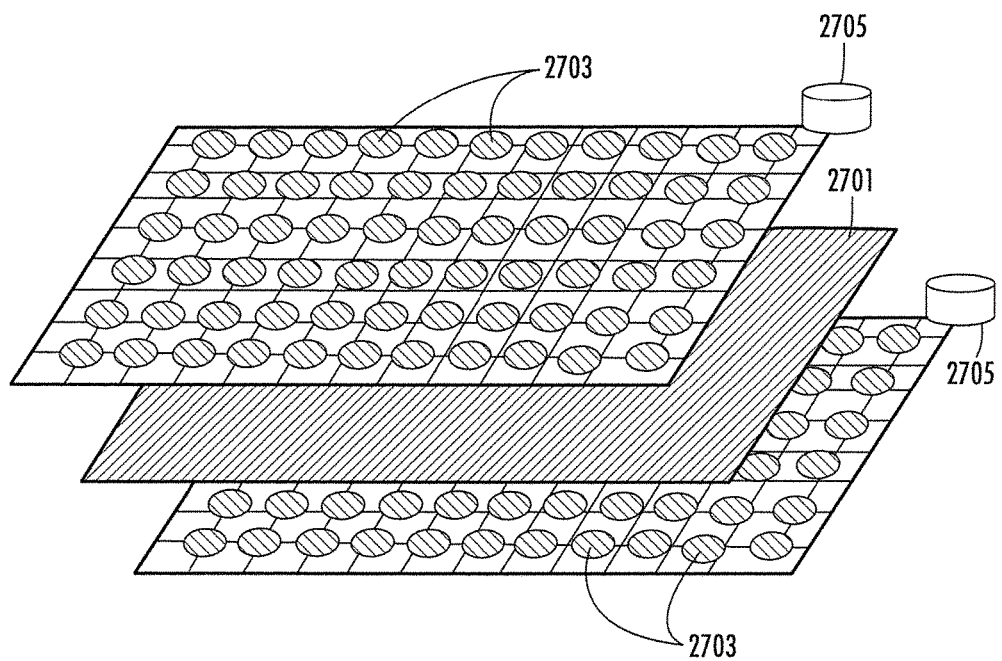
FIG. 24 shows a test setup for a leak test.

FIG. 24 shows yet another configuration of the computer system for improving the reliability of an integrity or leak test of a sample 2701. In the example of FIG. 24, the sample 2701 is a two-dimensional bag. To set up the test, temperature sensor grids are arranged on each side of the sample 2701. Each temperature sensor grid includes temperature sensors 2703. Each temperature sensor grid may also include contacts 2705 to connect the temperature sensor grids to a test apparatus such as the test apparatus 2405.

Figure 25:
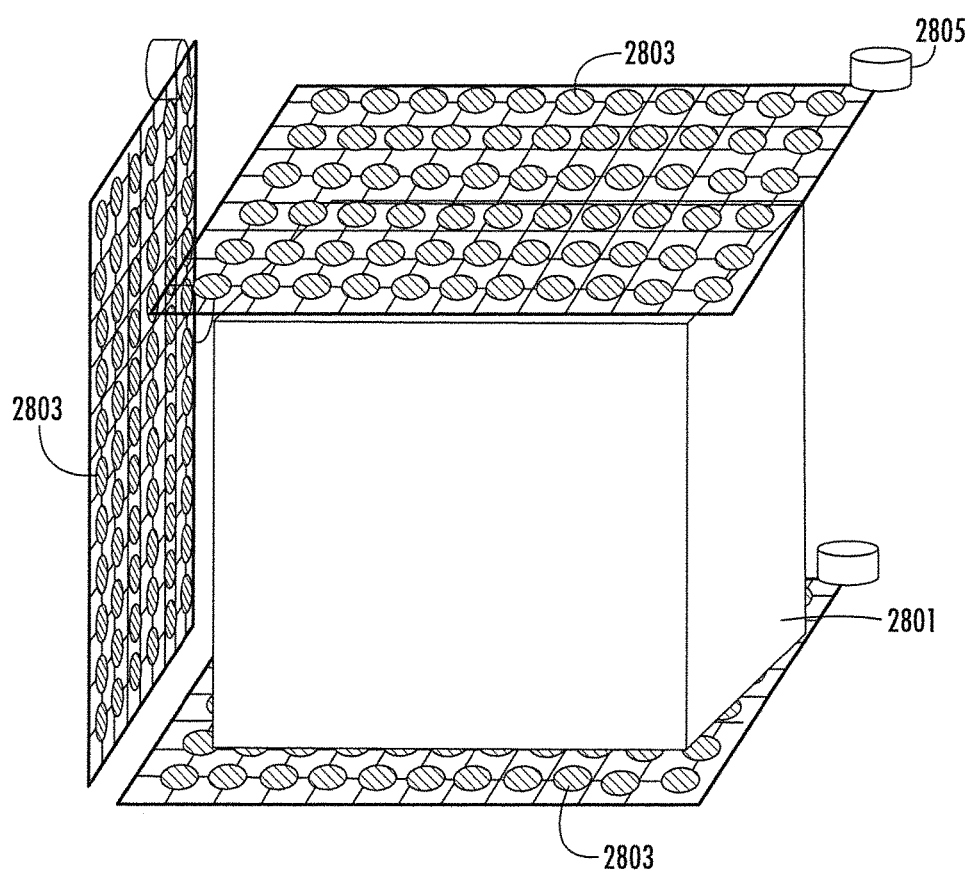
FIG. 25 shows yet another test setup for a leak test.

FIG. 25 shows yet another configuration of the computer system for improving the reliability of an integrity or leak test of a sample. According to the example, a sample 2801 is a three-dimensional bag. Temperature sensor grids are arranged on all six sides of the sample 2801 (only three temperature sensor grids are shown). Each temperature sensor grid includes temperature sensors 2803. Each temperature sensor grid further includes contacts 2805 or a connection to a test apparatus, such as the test apparatus 2405. The connection may be implemented via cable or wireless means.

Figure 26:
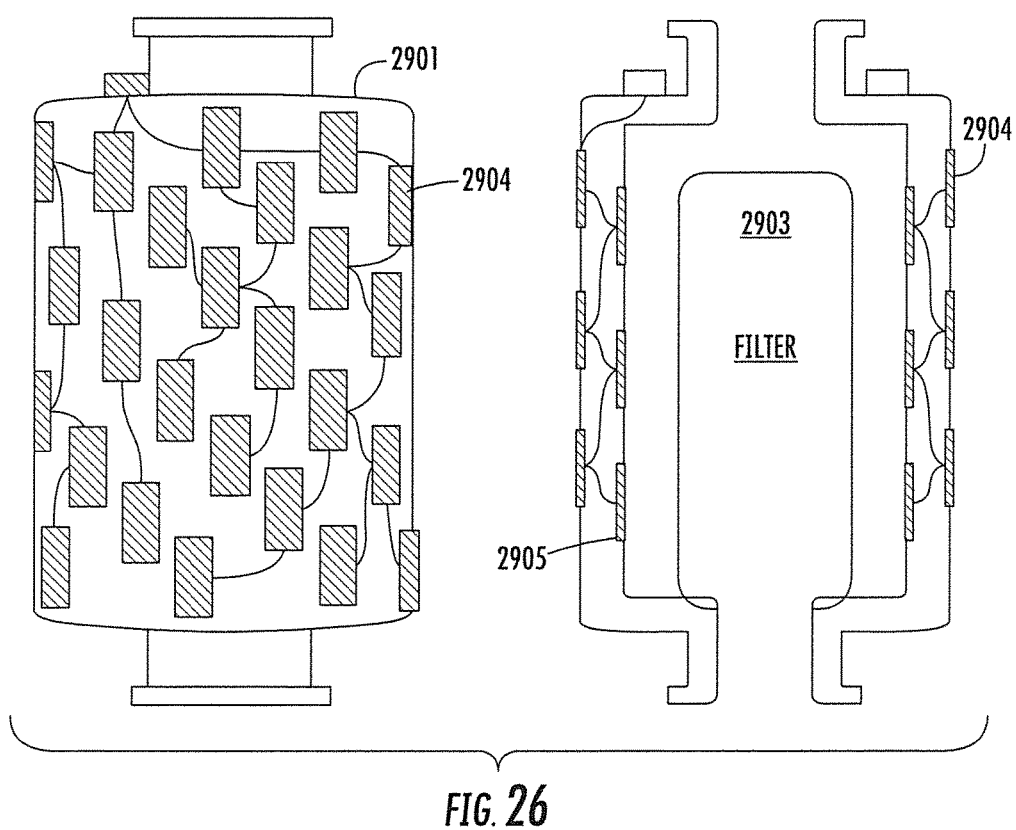
FIG. 26 shows another test setup for an integrity test.

FIG. 26 shows yet another configuration of the computer system for improving the reliability of an integrity or leak test of a sample. According to the example, a sample 2901 is implemented as a filter capsule including a filter element 2903. The sample 2901 may be manufactured with external temperature sensors 2904 mounted to the wall of the sample

2901. The sample 2901 may also be manufactured with humidity sensors mounted to its wall. In addition, internal temperature sensors 2905 may be mounted to an inner wall of the sample 2901. External sensors 2904 of the sample 2901 may include temperature sensors and/or humidity sensors.

In the examples of FIGS. 21 to 26, when several temperature or humidity sensors are used, their respective locations may be identified. Accordingly, it may be possible, e.g. with the test apparatus 2405 or the external device 2501, to determine which part of the sample is affected by a deviation. In other words, by knowing the location from which values determined using a temperature sensor are received, localization of deviations from a specified temperature or a specified humidity may be determined. Further, once the localization has been determined, the localization may be used to determine the extent of an impact on an assessment of the integrity of the sample caused by the deviation, e.g. to correct for the impact or to generate a corresponding error message.

FIGS. 27 to 32 show an interface that may be used to interact with the computer system for improving the reliability of an integrity or leak test of a sample.

FIG. 27 shows various parameters that may be selected by a user. In particular, the user may select whether an assessment of the integrity of the sample that is affected by a deviation should be corrected in real time or post-test, i.e. after the test is complete. Alternatively, the user may select a risk assessment if the assessment of the integrity of the sample should not be corrected. The user can also select trend analysis in addition to the other options. The selection of trend analysis may enable the use of a maximum expected change in the assessment of the integrity of the sample under specified conditions to be used to evaluate whether the deviation (e.g. from a temperature determined under specified temperature conditions) has an impact on whether the second assessment indicates a passed test or a failed test.

Regardless of whether the user selects real time correction, post-test correction, or risk assessment, a comprehensive report of the test may be generated.

Figure 28:
FIG. 28 shows another interface for the apparatus.

FIG. 28 shows another aspect of the interface that may be used to interact with the computer system for improving the reliability of an integrity test or leak test of a sample. In the example of FIG. 28, the sample may be indicated via a keyword. The sample is referred to as the system to be tested. According to the example, "bag 50L" is a keyword that specifies a 50 liter bag.

FIG. 29 shows an interface that may be displayed after selecting a search function of FIG. 28. Accordingly, upon searching for a 50 liter bag, two alternative choices are displayed. In particular, a "Flexboy 50L with constraining plates" and a "STR 50L installed bag". The user may select one of the two alternatives.

Figure 30:
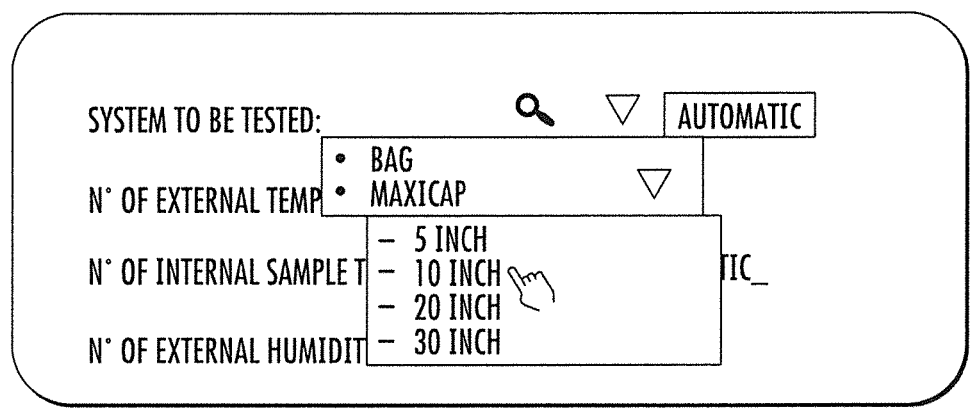
FIG. 30 shows a further interface for the apparatus.

As an alternative to the process of FIGS. 28 and 29, FIG. 30 shows that the sample can be selected from a drop down menu.

Figure 31:
FIG. 31 shows a further interface for the apparatus.

FIG. 31 shows the use of automatic detection of the sample. In particular, automatic detection may be used if sensors are incorporated into the sample or a jacket with sensors is used, as discussed above. If automatic detection is selected, the numbers of sensors and their locations are automatically retrieved upon connection to the sensors.

Figure 32:
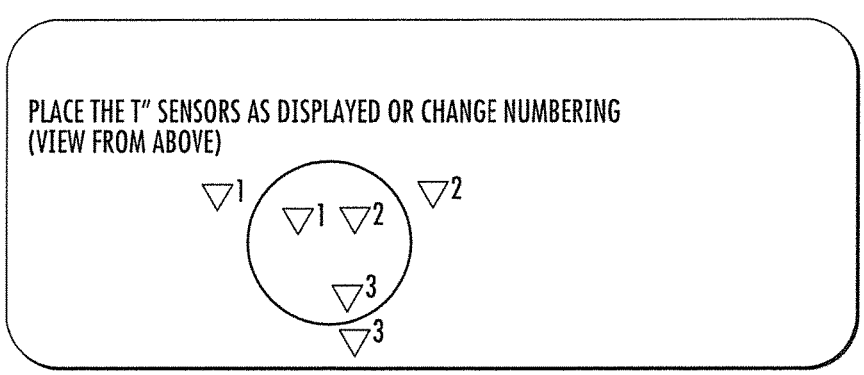
FIG. 32 shows two further interfaces for the apparatus.
Figure 32:
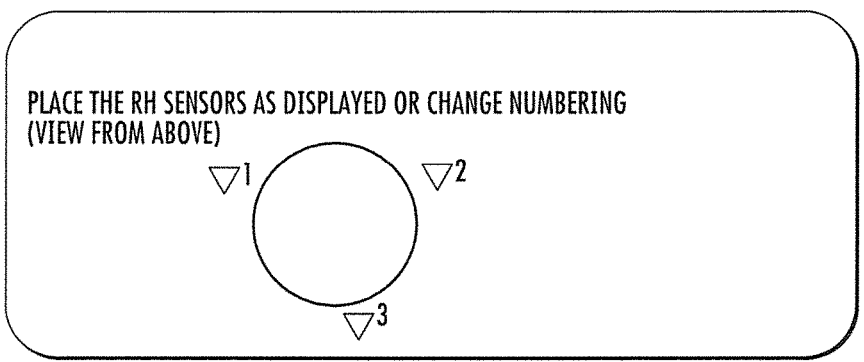

FIG. 32 shows another interface for the computer system for improving the reliability of an integrity or lead test of a sample. According to the example of FIG. 32, automatic detection is not selected. Accordingly, the number of temperature sensors and their location may be manually defined. In addition, the number of humidity sensors and their locations may be manually defined.

Figure 33:
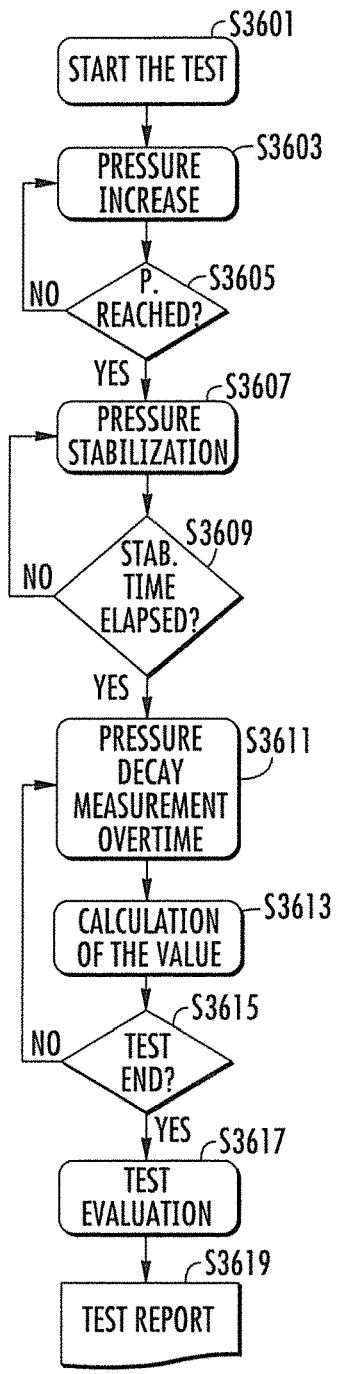
FIG. 33 shows a conventional method for carrying out an integrity test.

FIG. 33 shows a conventional approach for performing an integrity test. In the example of FIG. 33, a diffusion test is performed. At the start of the test S3601, the test apparatus 2405 may run a function test during which operating pressure and current barometric pressure are determined. Afterwards, the testing apparatus 2405 may check whether an external reference tank is connected for testing large volume systems. If so, the inlet volume of the test system may be determined using this reference tank.

At step S3603 test pressure is built up to a user defined value. At step S3605 a check may be performed to determine whether the test pressure has built up to the user defined value. If this is not the case, the pressure is increased. At step S3607, pressure stabilization takes place to attain constant test conditions. At step S3609, the pressure is monitored until pressure stabilization can be ensured. At step S3611 a pressure drop test may begin. During the pressure drop test, the rate of diffusion may be continuously calculated at step S3613. At the end of a predefined test period, the end of the integrity test may be determined at step S3615. An evaluation of the test may be carried out at step S3617. A report of the test, possibly including an indication of a passed test or a failed test, may be provided at step S3619. In addition, results of assessments of the integrity of the sample taken during the test may be provided in the test report.

Figure 36:
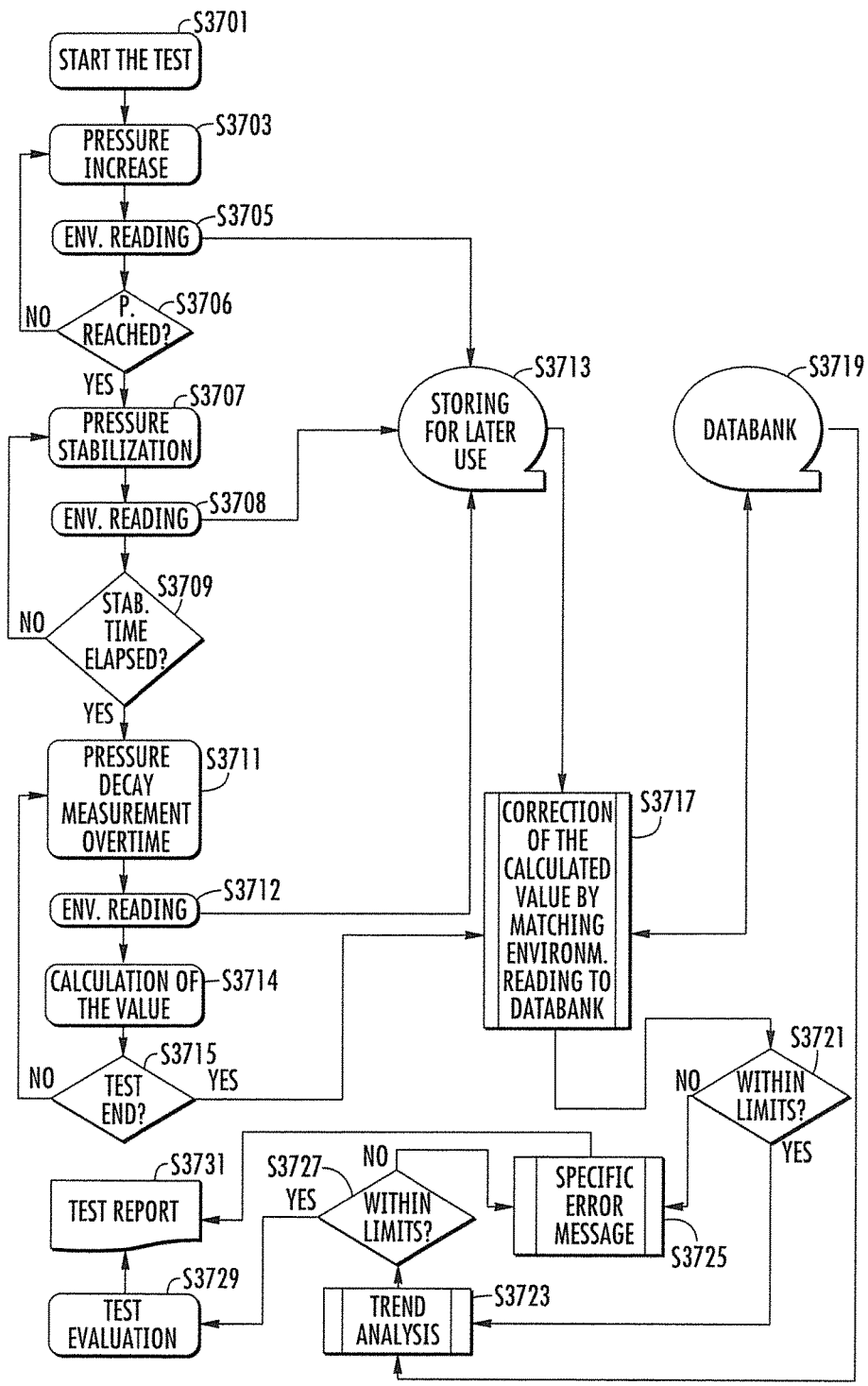
FIG. 36 shows another variation of the approach for carrying out the integrity test according to the embodiment.

FIG. 36 shows a process carried out according to aspects disclosed in the present application. In particular, an integrity test of a filter is carried out. Step S3701 may be carried out similarly to step S3601. Further, step S3703 may be similar to step S3603. At step S3705 an environmental reading is obtained. The environmental reading may be obtained via a plurality of sensors arranged around or within the sample being tested. Step S3706 may be carried out similarly to step S3605. Further, step S3707 may be carried out similarly to step S3607.

At step S3708, a further environmental reading may be obtained. The environmental reading may be obtained using a plurality of sensors arranged around or within the sample. Step S3709 may be carried out similarly to step S3609. Further, step S3711 may be carried out similarly to step S3611. At step S3712, an environmental reading of the environment of the sample may be obtained. The environmental reading may be obtained using a plurality of sensors arranged around or within the sample. The plurality of sensors may include a temperature sensor and/or a humidity sensor. The environmental readings obtained at steps S3712, S3708 and S3705 may be stored for later use at step S3713. The readings may be stored in the database. At step S3714, a rate of diffusion may be calculated as described in step S3613. Step S3715 may be similar to step S3615.

Each environmental reading carried out at steps S3705, S3708, and S3712 may include determining at least one first parameter indicative of at least one of the following: a first volume of the sample, a first pressure of the sample, a first temperature of the sample, and a first assessment of the integrity of the sample.

Step S3715 may include determining an indication provided by an assessment of the integrity of the sample taken at the end of the test period. In one of steps S3705, S3708, and S3712, at least one second parameter indicative of a deviation from the first parameter may be determined. A determination whether the deviation has an impact on the assessment of the integrity of the sample taken at the end of the test period may be carried out at step S3717. When the deviation is determined to have an impact on the indication of the assessment, the assessment may be corrected. In particular, the assessment of the integrity of the sample taken at the end of the test period may be corrected in view of previously recorded reactions to different environmental conditions recorded for the specific sample. The previously recorded reactions may be retrieved from the database at step S3719.

If the assessment of the integrity of the sample is determined to be within correctable limits at step S3721, a trend analysis may be carried out at step S3723. Alternatively, if the assessment cannot be corrected, a specific error message may be generated at step S3725. The trend analysis may be carried out as discussed above. If the assessment of the integrity of the sample carried out at the end of the test period differs from a first assessment of the integrity of the sample carried out under specified environmental conditions by a quantity greater than a maximum expected change associated with the sample, a determination is made at step S3727 to generate a specific error message. However, if the quantity is less than the maximum expected change then the process proceeds to steps S3729 and S3731. Step S3729 may be similar to step S3617. Step S3731 may be similar to step S3619.

The maximum expected change may be determined as discussed above.

Figure 35:
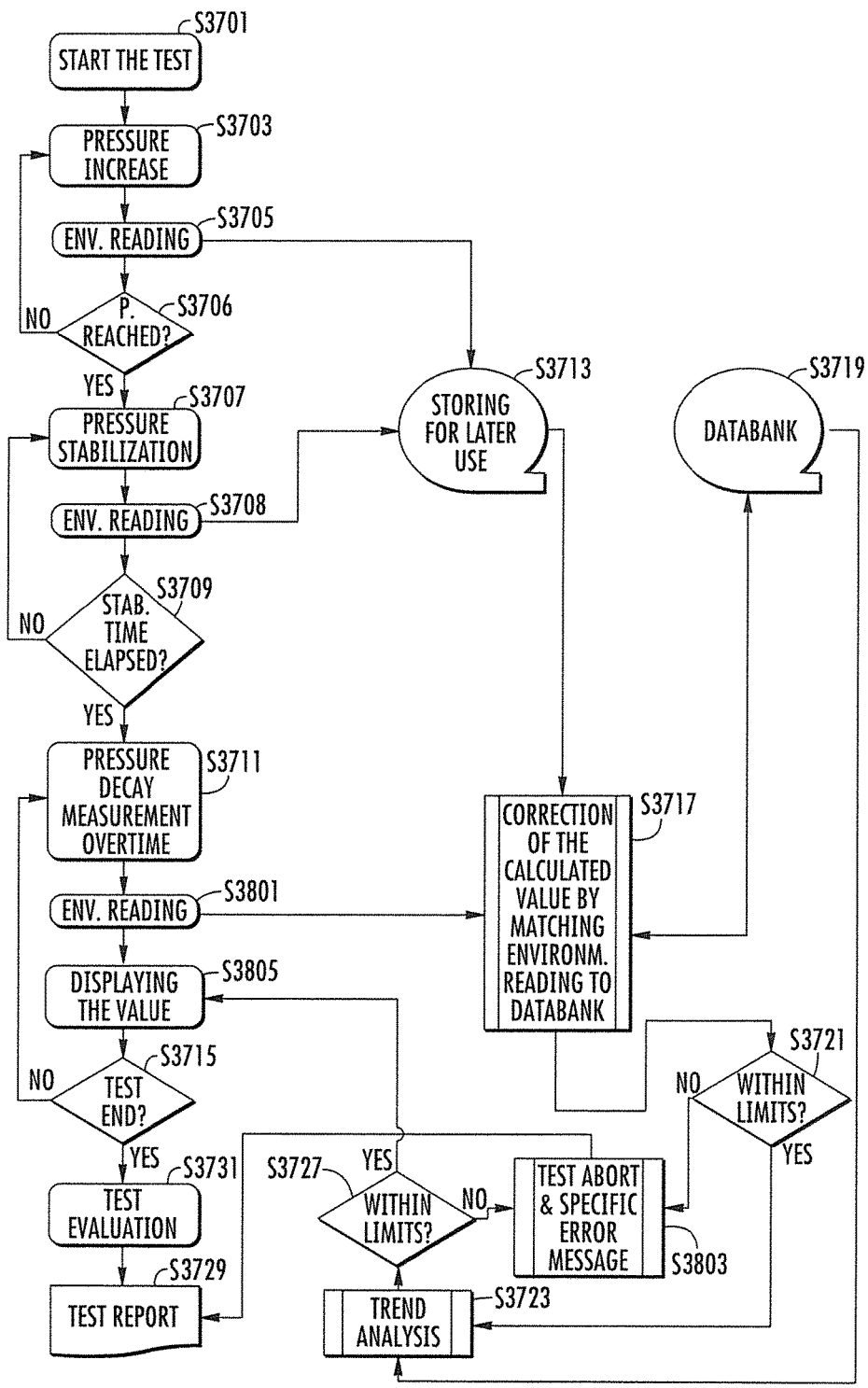
FIG. 35 shows a variation of the approach for carrying out the integrity test according to the embodiment.

FIG. 35 shows another implementation for the method of improving the reliability of an integrity test or a leak test of a sample. The process of FIG. 35 is similar to FIG. 36, except that FIG. 35 includes real-time correction of the test value, i.e. the maximum diffusion rate, as opposed to the post correction of the test value carried out in the context of FIG. 36.

Many of the steps shown in FIG. 35 are carried out according to the description of FIG. 36. However, there are some differences, as follows. At step S3801, in contrast to step S3712, the environmental reading is sent for evaluation at step S3717, rather than being stored for later use.

For example, at one of steps S3705 or S3708, at least one first parameter may be determined. The first parameter may be indicative of at least one of the following: a first volume of the sample, a first temperature of the sample, a first pressure of the sample, a first assessment of the integrity of the sample. The first parameter may be determined under specified environmental conditions, e.g. stable temperature and/or humidity conditions.

At step S3801 (similar to step S3712), at least one second parameter may be determined. The at least one second parameter may be indicative of a deviation from the first parameter.

Further, after the determination of the at least one second parameter, at least one third parameter indicative of a second assessment of the integrity of the sample may be determined.

At Step S3721, instead of generating an error message if a second rate of diffusion determined as the second assessment of the integrity of the sample is not correctable, the test may be aborted and an error message may be generated at step S3803. For example, if the rate of diffusion determined as the second assessment of the integrity of the sample differs by too great an extent from a first rate of diffusion determined as the first assessment of the integrity of the sample, the second rate of diffusion is not correctable.

At step S3727, instead of moving to a test evaluation step if the trend analysis of step S3723 determines that the second rate of diffusion does not deviate from the first rate of diffusion by more than the maximum expected change, the process of FIG. 35 moves to step S3805, and a corrected second rate of diffusion is displayed. The second rate of diffusion may be corrected based on analysis of the effects of various environment conditions on the sample, as discussed above.

Figure 34:
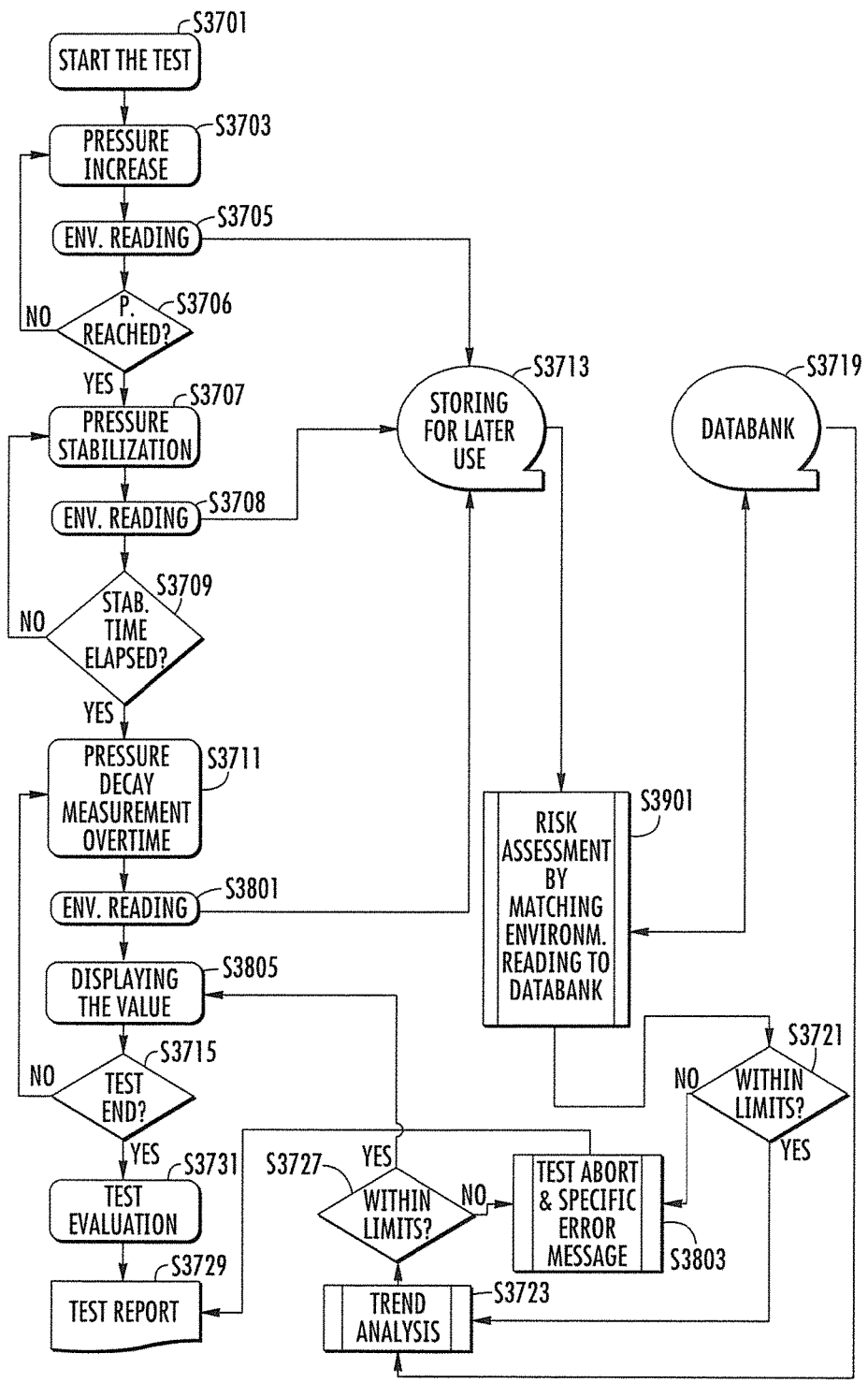
FIG. 34 shows an approach for carrying out an integrity test according to an embodiment.

FIG. 34 shows another implementation for the method of improving the reliability of an integrity test or a leak test of a sample. The process of FIG. 34 is similar to the process of FIG. 36. However, instead of step S3717, step S3901 is carried out. Accordingly, rather than a correction of the second rate of diffusion determined as the second assessment of the integrity of the sample, a risk assessment is performed by evaluating the second rate of diffusion. For example, the risk may be higher depending of the degree to which the second rate of diffusion differs from the first rate of diffusion. Other risk assessments are also possible.

Figure 37:
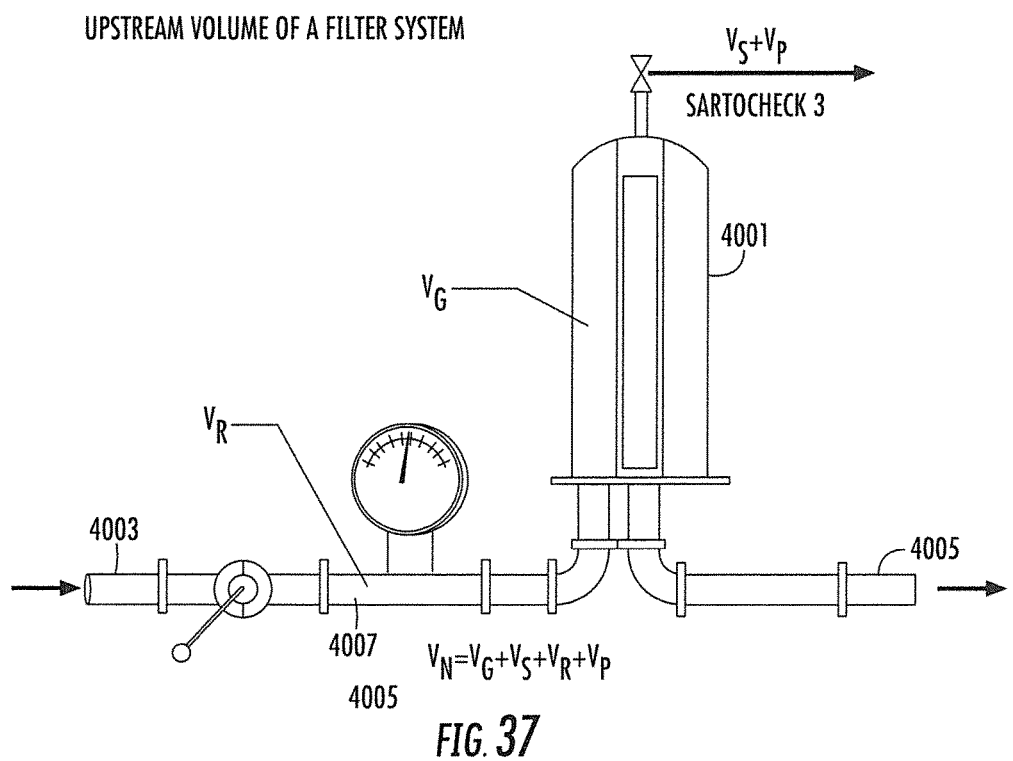
FIG. 37 shows an exemplary filter system in which the method of improving the reliability of an integrity or leak test of a sample may be carried out.

FIG. 37 shows an exemplary filter system in which the method of improving the reliability of an integrity or leak test of a sample may be carried out.

The filter system includes a sample 4001 (a filter capsule in this case), an upstream pipe 4003 and a downstream pipe 4005. The downstream pipe 4005 may include a downstream valve.

An integrity test method performed using the filter system may be based on a determination of the pressure drop on the upstream side of the filter system.

In some cases, the pressure drop can be used directly as an assessment of the integrity of the sample 4001, provided that the system's upstream volume is constant or known.

Rate of diffusion may provide a more reliable assessment of the integrity of the sample 4001. The rate of diffusion can be calculated from the pressure drop, the upstream volume of the filter system and the test time, e.g. the number of minutes since the test began. The calculated rate of diffusion allows direct correlation, which is independent of a filter system's upstream volume, with the actual retention capability of the sample 4001.

The upstream volume of the filter system may be determined at point 4007. The determination of the upstream volume can be carried out according to conventional techniques, e.g. using Boyle's law.

When pressure is applied to the upstream side of a wet filter element of the sample 4001, a diffuse gas stream starts to flow through a filter membrane of the filter element after a short time.

In the context of a diffusion test, the rate of diffusion of the filter element can be calculated as follows from the pressure drop, test time, upstream system volume and the reference pressure ("$p_0$"=1000 mbar), according to German industrial standard DIN 58356, Part 2:

$$D = \frac{p_1 \cdot V_1}{p_0 \cdot t} \cdot \ln\left[\frac{p_1}{p_1 - \Delta p}\right] \text{ [ml/min]}$$

D=Rate of Diffusion in ml/min
$p_1$=Test pressure in mbar at the beginning of a test
$\Delta p = p_1 - p_2$ (pressure at the end of a test) in mbar
$V_1$=Upstream volume of the filter system in ml
t=Test time in minutes (i.e. time that has passed since the start of the test)
$p_0$=1000 mbar (or actual determined barometric pressure)

The rate of diffusion may be calculated in reference to a constant test pressure and is independent of the filter system's volume so that a direct correlation with the actual retention capability of the filter element is given.

Other mechanisms of calculating the rate of diffusion may also be used.

Figure 38:
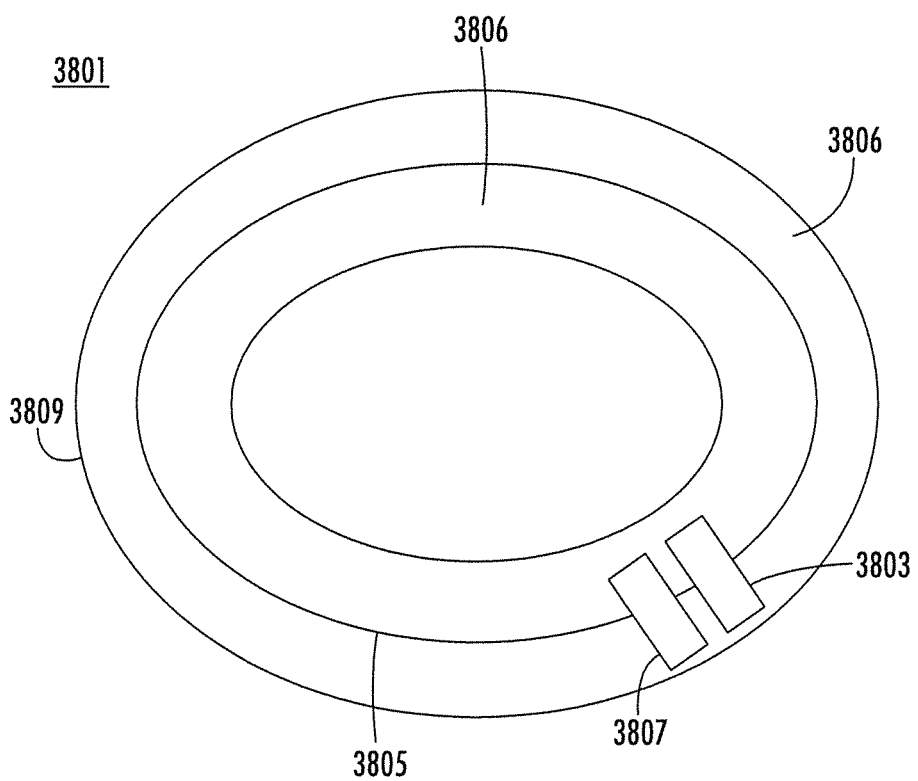
FIG. 38 shows a tension sensor.

FIG. 38 shows a tension sensor 3801. The tension sensor 3801 can be used for determining the parameters discussed above (e.g., the first parameter, the second parameter, the third parameter). More specifically, the tension sensor 3801 may be implemented using a capsular tension ring.

For example, the tension sensor 3801 may use radio frequency for power and/or data transfer. Accordingly, a chip 3803 may be provided for radio frequency power transfer, temperature to frequency conversion and external communication.

Further, the tension sensor 3801 may include an antenna 3805 (e.g., a coil antenna). The antenna 3805 may have a circular or ring shape. The antenna 3805 may be enclosed in an insulating material 3806. The insulating material may be made from a polymer, e.g., a flexible elastomer.

Also, the tension sensor 3801 may include a pressure sensor 3807, e.g., capacitive or electromagnetic. A change in pressure may cause a corresponding change in capacitance in the pressure sensor 3807. The change in capacitance may be converted into a change in frequency, e.g., via an oscillator of the chip 3803. The change in frequency may be transmitted to an external device as an encoded signal, e.g., via radio frequency backscatter.

The tension sensor 3801 may include a temperature sensor (not shown). The tension sensor may be enclosed in an external ring 3809. The external ring 3809 may be made from a polymer, such as polyurethane.

The tension sensor 3801 may be integrated into or may encompass one of the samples described above, e.g., the sample 4001. Accordingly, as temperature increases, the sample 4001 expands and the tension increases. As the temperature decreases, the sample 4001 contracts and the tension decreases. This relationship is described in the following equation:

$$f(\Delta \text{tension}) = \Delta \text{volume}$$

The tension sensor 3801 may be used to determine the change in volume of the sample 4001. The tension sensor 3801 may be used to correct an indirect volume determination. For example, if a volume of the sample 4001 is determined according to the correspondence table, as described above, such a determination may not account for pressure. More particularly, if an initial volume is determined at a relatively low pressure, higher test pressures could lead to expansion of the sample 4001, and a corresponding increase in volume. This increase might not be reflected in the determination of volume according to the correspondence table, but would be determined via the tension sensor 3801.

What is claimed is:

1. A computer-implemented method for improving reliability of an integrity or leak test of a sample, the method comprising:
   determining at least one first parameter indicative of a first temperature of the sample;
      wherein the at least one first parameter is determined under specified temperature conditions;
   determining at least one second parameter indicative of a deviation from the first parameter;
   determining, after determining the at least one second parameter, at least one third parameter indicative of an assessment of the integrity of the sample,
   wherein the assessment provides an indication of a passed test or a failed test;
   determining whether the deviation has an impact on the indication provided by the assessment based on one or more of the following factors:
      thermal characteristics of the sample,
      efficiency of heat transfer to or from the sample wall,
      environmental humidity,
      geometry of the sample,
      speed and amount of thermal expansion or contraction of the sample according to localized environmental deviations,
      thermal capacity or thermal conductivity of the sample wall,
      a maximum expected change in the assessment of the integrity of the sample under stable temperature conditions; and wherein,
      when the deviation is determined to have an impact on the indication provided by the assessment, identifying a possibility that the indication provided by the assessment is incorrect.

2. The method of claim 1, wherein the deviation comprises a deviation from a first temperature of the sample that causes a corresponding deviation from the first volume of the sample.

3. The method of claim 1, wherein each parameter is determined based on a measurement of the sample or a measurement of an environment of the sample,
   wherein each parameter is based on measurements taken during the test,
   wherein the at least one first parameter and the at least one second parameter are based on a temperature of the sample or another measurement indicative of the temperature;
   wherein a first temperature of the sample is indicative of the first volume of the sample;
   wherein the deviation from the first volume is determined based on a temperature or tension of the sample.

4. The method of claim 1, wherein the at least one first parameter includes at least three parameters, wherein a plurality of the at least three parameters are indicative of a first assessment of the integrity of the sample,
   wherein the plurality of parameters include a measured change in a pressure of the sample,
   wherein the measured change in pressure is used to calculate a rate of diffusion of the sample,
   wherein each assessment of the integrity of the sample is a rate of diffusion of the sample.

5. The method of claim 1, wherein the determination of whether the deviation has an impact on the indication is based further on one or more of the following:
   a rate of heat transfer to or from the sample;
   a change in the volume of the sample with respect to the first volume.

6. The method of claim 5, wherein the heat transfer to or from the sample and/or the change in volume of the sample are determined based on one or more of the following:
   characteristics of the sample;
   localization of the deviation from the first temperature of the sample;
   an intermediate volume between a filter element of the sample and an inner wall of a housing of the sample;
   a composition and position of a holder of the sample;
   a humidity of an environment of the sample;
   a tension of the sample.

7. The method of claim 5, wherein the change in the volume of the sample and the rate of heat transfer to or from the sample are determined when the second assessment is determined.

8. The method of claim 7, wherein the impact on the indication of the second assessment comprises at least one of an impact resulting from the change in the volume and an impact resulting from the rate of heat transfer to or from the sample.

9. The method of claim 1, further comprising a first step of establishing characteristics of the sample, wherein the characteristics of the sample include thermal characteristics, wherein the thermal characteristics comprise one or more of the following: a coefficient of thermal expansion, a specific heat, a thermal inertia.

10. The method of claim 9, wherein the characteristics of the sample further include design characteristics, wherein the design characteristics include at least one of dimensions, geometry, material composition, a wall thickness, pore size, type of sample, a maximum rate of diffusion, a maximum pressure.

11. The method of claim 9,
wherein the sample is a bag or a filter, particularly a sterilizing filter;
wherein the filter includes a housing and an element inside the housing;
wherein the element is a filter cartridge or
wherein the element is a membrane.

12. The method of claim 9,
wherein the test is an integrity test, wherein the test includes one or more of the following:
a diffusion test;
a pressure drop test;
a bubble point test;
a water intrusion test;
an aerosol challenge test.

13. A computer program product, tangibly embodied in a computer-readable medium, comprising computer readable instructions, which, when executed on a computer system, cause the computer system to perform the following operations:
determining at least one first parameter indicative of a first volume of the sample;
wherein the at least one first parameter is determined under specified temperature conditions;
determining at least one second parameter indicative of a deviation from the first parameter;
determining, after determining the at least one second parameter, at least one third parameter indicative of an assessment of integrity of the sample,
wherein the assessment provides an indication of a passed test or a failed test;
determining whether the deviation has an impact on the indication provided by the assessment based on one or more of the following factors:
thermal characteristics of the sample,
efficiency of heat transfer to or from the sample wall,
environmental humidity,
geometry of the sample,
speed and amount of thermal expansion or contraction of the sample according to localized environmental deviations,
thermal capacity or thermal conductivity of the sample wall,
a maximum expected change in the assessment of the integrity of the sample under stable temperature conditions; and wherein,
when the deviation is determined to have an impact on the indication provided by the assessment, identifying a possibility that the indication provided by the assessment is incorrect.

14. A computer system for improving reliability of an integrity or leak test of a sample, comprising:
a plurality of sensors arranged around or within the sample,
wherein the sensors are operable to determine at least one first parameter indicative of at least one of a first volume of the sample;
wherein the at least one first parameter is determined under specified temperature conditions; and
the sensors being operable to determine at least one second parameter indicative of a deviation from the first parameter;
after determining the at least one second parameter, the sensors are operable to determine at least one third parameter indicative of an assessment of the integrity of the sample,
wherein the assessment provides an indication of a passed test or a failed test;
a processor to:
determine whether the deviation has an impact on the indication provided by the assessment based on one or more of the following factors:
thermal characteristics of the sample,
efficiency of heat transfer to or from the sample wall,
environmental humidity,
geometry of the sample,
speed and amount of thermal expansion or contraction of the sample according to localized environmental deviations,
thermal capacity or thermal conductivity of the sample wall,
a maximum expected change in the assessment of the integrity of the sample under stable temperature conditions; and wherein,
when the deviation is determined to have an impact on the indication provided by the assessment, identify a possibility that the indication provided by the assessment is incorrect.

* * * * *